(12) United States Patent
García Collazo et al.

(10) Patent No.: US 9,782,395 B2
(45) Date of Patent: Oct. 10, 2017

(54) 2,4-THIAZOLIDINEDIONE DERIVATIVES IN THE TREATMENT OF CENTRAL NERVOUS SYSTEM DISORDERS

(71) Applicant: MINORYX THERAPEUTICS S.L., Mataró, Barcelona (ES)

(72) Inventors: Ana María García Collazo, Barcelona (ES); David John Augustus Eckland, Watford (GB); Maria Pilar Pizcueta Lalanza, Barcelona (ES); Marc Martinell Pedemonte, Barcelona (ES)

(73) Assignee: MINORYX THERAPEUTICS S.L., Mataró, Barcelona (ES)

(*) Notice: Subject to any disclaimer, the term of this patent is extended or adjusted under 35 U.S.C. 154(b) by 0 days.

(21) Appl. No.: 15/147,484

(22) Filed: May 5, 2016

(65) Prior Publication Data

US 2016/0235729 A1    Aug. 18, 2016

Related U.S. Application Data

(63) Continuation of application No. PCT/EP2015/057224, filed on Apr. 1, 2015.

(30) Foreign Application Priority Data

Apr. 2, 2014  (EP) .................................. 14382130

(51) Int. Cl.
| | | |
|---|---|---|
| C07D 401/02 | (2006.01) | |
| A61K 31/4439 | (2006.01) | |
| A61K 9/00 | (2006.01) | |
| A61K 9/08 | (2006.01) | |
| A61K 9/10 | (2006.01) | |
| C07D 417/12 | (2006.01) | |
| A61K 45/06 | (2006.01) | |

(52) U.S. Cl.
CPC ........ *A61K 31/4439* (2013.01); *A61K 9/0053* (2013.01); *A61K 9/08* (2013.01); *A61K 9/10* (2013.01); *A61K 45/06* (2013.01); *C07D 417/12* (2013.01)

(58) Field of Classification Search
CPC .......................... C07D 417/00; A61K 31/4439
USPC ........................................ 514/342; 546/269.7
See application file for complete search history.

(56) References Cited

U.S. PATENT DOCUMENTS

| | | |
|---|---|---|
| 5,441,971 A | 8/1995 | Sohda et al. |
| 6,100,403 A | 8/2000 | Saito et al. |
| 6,191,154 B1 | 2/2001 | Landreth et al. |
| 6,294,192 B1 | 9/2001 | Patel et al. |
| 6,451,339 B2 | 9/2002 | Patel et al. |
| 6,720,001 B2 | 4/2004 | Chen et al. |
| 8,389,556 B2 | 3/2013 | Colca et al. |
| 8,722,710 B2 | 5/2014 | Czarnik |
| 8,865,747 B2 | 10/2014 | Pujol Onofre |
| 8,895,536 B2 | 11/2014 | Bannister et al. |
| 8,895,537 B2 | 11/2014 | Bannister et al. |
| 8,969,581 B2 | 3/2015 | DeWitt |
| 2013/0274295 A1* | 10/2013 | Pujol Onofre ..... A61K 31/4439 514/342 |
| 2014/0088127 A1 | 3/2014 | Pandey et al. |
| 2014/0178456 A1 | 6/2014 | Devanaboyina |
| 2014/0243377 A1 | 8/2014 | Czarnik |
| 2014/0275180 A1 | 9/2014 | DeWitt |
| 2015/0224120 A1 | 8/2015 | Clelland et al. |
| 2015/0284346 A1 | 10/2015 | DeWitt |

FOREIGN PATENT DOCUMENTS

| | | |
|---|---|---|
| EP | 1 465 627 B1 | 3/2006 |
| EP | 1 133 294 B1 | 8/2010 |
| WO | WO 92/18501 A1 | 10/1992 |
| WO | WO 93/22445 A1 | 11/1993 |
| WO | WO 2013/040419 A1 | 3/2013 |
| WO | WO 2014/152843 A1 | 9/2014 |
| WO | WO 2015/109037 A1 | 7/2015 |

OTHER PUBLICATIONS

WHO "Classification of mental disorder" p. 1-268 (1993).*
Class of mental disorder, WHO guidllines p. 1-268 (1993).*
LeoniLeoni et al. "Novel thiazole . . . " Exp. Opin. ther. Patents 24(7) 759-777 (2014).*
Garattini "Active drug metabolites . . . " Clin. Pharmacokinetics 10, p. 216-227 (1985).*
CINAPS Dossier "Pioglitazone" p. 1-21 (2009).*
Lin et al. "Simultaneous determ . . . " J. Pharm. Biomed. Analysis 33, 0.101-108 (2003).*
USPTO "guidance for determining subject matter . . . " p. 1-5 Fed. Cir (2014).*
Barter, Z.E., et al., "Scaling Factors for the Extrapolation of In Vivo Metabolic Drug Clearance From in Vitro Data: Reaching a Consensus on Values of Human Microsomal Protein and Hepatocellularity Per Gram of Liver," *Current Drug Metabolism* 8(1):33-45, Bentham Science Publishers Ltd., Netherlands (2007).
Baxter, A.G., "The Origin and Application of Experimental Autoimmune Encephalomyelitis," *Nature Reviews Immunology* 7(11):904-912, Nature Publishing Group, England (2007).
Callizot, N., et al., "Operational Dissection of β-Amyloid Cytopathic Effects on Cultured Neurons," *Journal of Neuroscience Research* 91(5):706-716, Wiley Periodicals, Inc., United States (2013).
Fourcade, S., et al., "Mitochondrial Dysfunction and Oxidative Damage Cooperatively Fuel Axonal Degeneration in X-linked Adrenoleukodystrophy," *Biochimie* 98:143-149, Elsevier Masson SAS, France (2014) (Published online 2013).
Hansen, M.B., et al., "Re-examination and Further Development of a Precise and Rapid Dye Method for Measuring Cell Growth/Cell Kill," *Journal of Immunological Methods* 119(2):203-210, Elsevier, Netherlands (1989).

(Continued)

*Primary Examiner* — Zinna Northington-Davis
(74) *Attorney, Agent, or Firm* — Sterne, Kessler, Goldstein & Fox PLLC

(57) ABSTRACT

The present invention provides 5-(4-(2-(5-(1-hydroxyethyl) pyridine-2-yl)ethoxy) benzyl)thiazolidine-2,4-dione and novel stereoisomers of said compound for use in the treatment of central nervous system (NS) disorders.

22 Claims, 7 Drawing Sheets

(56) References Cited

OTHER PUBLICATIONS

International Search Report for International Application No. PCT/EP2015/057224, European Patent Office, Rijswijk, Netherlands, dated Jun. 15, 2015, 4 pages.
Itoh, T. and Yamamoto, K., "Peroxisome Proliferator Activated Receptor γ and Oxidized Docosahexaenoic Acids as New Class of Ligand," *Naunyn-Schmiedeberg's Arch. Pharmacol.* 377(4-6):541-547, Springer Verlag, Germany (2008).
Kostic, M., et al., "IL-17 and Glutamate Excitotoxicity in the Pathogenesis of Multiple Sclerosis," *Scandinavian Journal of Immunology* 79(3):181-186, John Wiley & Sons Ltd, England (Mar. 2014).
Lecluyse, E.L. and Alexandre, E., "Isolation and Culture of Primary Hepatocytes from Resected Human Liver Tissue," *Methods in Molecular Biology* 640:57-82, Humana Press, United States (2010).
Liu, S.-B. and Zhao, M.-G., "Neuroprotective Effect of Estrogen: Role of Nonsynaptic NR2B-containing NMDA Receptors," *Brain Research Bulletin* 93:27-31, Elsevier Inc., United States (2013) (Published online 2012).
Maeshiba, Y., et al., "Disposition of the New Antidiabetic Agent Pioglitazone in Rats, Dogs, and Monkeys," *Arzneim.-Forsch./Drug Res.* 47(1):29-35, Editio Cantor, Germany (1997).
Martinou, J.C., et al., "Cholinergic Differentiation Factor (CDF/LIF) Promotes Survival of Isolated Rat Embryonic Motoneurons in vitro," *Neuron* 8(4):737-744, Cell Press, United States (1992).
Mosmann, T., "Rapid Colorimetric Assay for Cellular Growth and Survival: Application to Proliferation and Cytotoxicity Assays," *Journal of Immunological Methods* 65(1-2):55-63, Elsevier Science Publishers B.V., Netherlands (1983).
Pujol, A., et al., "Functional Overlap between ABCD1 (ALD) and ABCD2 (ALDR) Transporters: A Therapeutic Target for X-adrenoleukodystrophy," *Human Molecular Genetics* 13(23):2997-3006, Oxford University Press, England (2004).
Schlüter, A., et al., "Functional Genomic Analysis Unravels a Metabolic-inflammatory Interplay in Adrenoleukodystrophy," *Human Molecular Genetics* 21(5):1062-1077, Oxford University Press, England (2012).
Schroeder, K., et al., "Ionworks™ HT: A New High-throughput Electrophysiology Measurement Platform," *Journal of Biomolecular Screening* 8(1):50-64, Sage Publications in association with The Society for Biomolecular Screening, United States (2003).
Singer, C.A., et al., "The Mitogen-Activated Protein Kinase Pathway Mediates Estrogen Neuroprotection after Glutamate Toxicity in Primary Cortical Neurons," *The Journal of Neuroscience* 19(7):2455-2463, Society for Neuroscience, United States (1999).
Sohda, T., et al., "Studies on Antidiabetic Agents. XII.[1)] Synthesis and Activity of the Metabolites of (±)-5-[p-[2-(5-Ethyl-2-pyridyl)ethoxy]benzyl]-2,4-thiazolidinedione (Pioglitazone)," *Chem. Pharm. Bull.* 43(12):2168-2172, Pharmaceutical Society of Japan, Japan (1995).
Sundararajan, S., et al., "PPARγ as a Therapeutic Target in Central Nervous System Diseases," *Neurochemistry International* 49(2):136-144, Elsevier Ltd, England (2006).
Tanis, S.P., et al., "Synthesis and Biological Activity of Metabolites of the Antidiabetic, Antihyperglycemic Agent Pioglitazone," *J. Med. Chem.* 39(26):5053-5063, American Chemical Society, United States (1996).
Wang, H. and Sieburth, D., "PKA Controls Calcium Influx into Motor Neurons During a Rhythmic Behavior," *PLoS Genetics* 9(9):e1003831:1-15, Public Library of Science, United States (2013).
Written Opinion for International Application No. PCT/EP2015/057224, European Patent Office, Munich, Germany, dated Jun. 15, 2015, 6 pages.
European Medicines Agency, "Guideline on the investigation of drug interactions," ema.europa.eu, accessed at http://www.ema.europa.eu/docs/en_GB/document_library/Scientific_guideline/2012/07/WC500129606.pdf, accessed on Mar. 14, 2016, 59 pages (Jun. 2012).
U.S. Department of Health and Human Services, "Guidance for Industry, Drug Interaction Studies—Study Design, Data Analysis, Implications for Dosing, and Labeling Recommendations," fda.gov, accessed at http://www.fda.gov/Drugs/GuidanceComplianceRegulatoryInformation/Guidances/default.htm, accessed on Mar. 14, 2016, 79 pages (Feb. 2012).
Takeda Chemical Industries, "ACTOS™ (Pioglitazone Hydrochloride) Tablets," NDA No. 21-073, drugbank.ca, accessed at http://www.drugbank.ca/system/fda_labels/DB01132.pdf?1265922797, accessed on Mar. 14, 2016, 26 pages (1999).
Extended European Search Report for European Patent Application No. 14382130.4, European Patent Office, Munich, Germany, dated May 28, 2014, 8 pages.
Jaakkola, T., et al., "Pioglitazone is Metabolised by CYP2C8 and CYP3A4 in vitro: Potential for Interactions with CYP2C8 Inhibitors," *Basic & Clinical Pharmacology & Toxicology* 99:44-51, Blackwell Munksgaard, Denmark (2006).
Vidal Medicinal preparations in Russia, "Pioglitazone," vidal.ru, accessed at https://www.vidal.ru/drugs/molecule/1253, accessed on Aug. 11, 2017, 3 pages.
English language machine translation of Vidal Medicinal preparations in Russia, "Pioglitazone," vidal.ru, accessed at http://www.vidal.ru/drugs/molecule/1253, accessed on Aug. 11, 2017, 3 pages.
WEB Project Group, "Pioglitazone," webapteka.ru, accessed at http://www.webapteka.ru/drugbase/inn2484.html, accessed on Aug. 11, 2017, 4 pages.
English language machine translation of WEB Project Group, "Pioglitazone," webapteka.ru, accessed at http://www.webapteka.ru/drugbase/inn2484.html, accessed on Aug. 11, 2017, 5 pages.

* cited by examiner

*p<0.05 one way ANOVA followed by Dunnett's test

*p<0.05 one way ANOVA followed by Dunnett's test

μ

SEQUENCE LISTING

<160> NUMBER OF SEQ ID NOS: 1

<210> SEQ ID NO 1
<211> LENGTH: 21
<212> TYPE: PRT
<213> ORGANISM: Artificial Sequence
<220> FEATURE:
<223> OTHER INFORMATION: myelin oligodendrocyte glycoprotein peptide
       35-55

<400> SEQUENCE: 1

Met Glu Val Gly Trp Tyr Arg Ser Pro Phe Ser Arg Val Val His Leu
1               5                   10                  15

Tyr Arg Asn Gly Lys
            20

2,4-THIAZOLIDINEDIONE DERIVATIVES IN THE TREATMENT OF CENTRAL NERVOUS SYSTEM DISORDERS

REFERENCE TO A SEQUENCE LISTING SUBMITTED ELECTRONICALLY VIA EFS-WEB

The content of the electronically submitted sequence listing (Name: 3746_0040001_SeqListing_ascii.txt; Size: 835 bytes; and Date of Creation: May 5, 2016) is herein incorporated by reference in its entirety.

FIELD OF THE INVENTION

This invention relates to novel uses of 2,4-thiazolidinedione derivatives as medicaments in particular for the treatment of central nervous system disorders.

BACKGROUND OF THE INVENTION

Central Nervous System (NS) disorders are diseases of any component of the brain and the spinal cord. NS disorders include disorders in which the nervous system is affected during the entire progression of the diseases such as neurodegenerative diseases (e.g., Alzheimer's disease, Huntington's chorea, Parkinson's disease, amyotrophic lateral sclerosis (ALS), degenerative ataxias such as Friedrich's ataxia, multiple sclerosis, multiple system atrophy and leukodystrophies), cerebrovascular diseases (e.g., global or local ischemia, intracerebral haemorrhage, stroke), seizures and epilepsy, viral diseases (e.g., meningitis, encephalitis), brain tumors and neuroinflammatory diseases. NS disorders also include disorders in which the nervous system is only affected during the latest stages of the development of the disorder. These disorders comprise rare metabolic diseases such as organic acidemias or fatty acid disorders and genetic mitochondrial disorders.

Neurodegenerative diseases are characterised by the progressive loss of structure or function of neurons, including death of neurons. These conditions are progressive and often fatal. The process of neurodegeneration is not well understood and the diseases that stem from it have, as yet, no cures in spite of treatments being constantly sought.

Some neurodegenerative diseases also include an inflammatory component, such as multiple sclerosis which traditionally was considered as inflammatory mediated demyelinating diseases but, in fact, is a neurodegenerative disease in which axonal damage, neuronal death and atrophy of the central NS are the principal causes of irreversible neurological disability in patients. Thus, multiple sclerosis can be considered as a neurodegenerative disease but also as a neuroinflammatory disease or autoimmune disease.

Leukodystrophies are a group of generic NS disorders whose main feature is the degeneration of the white matter in the brain. One disorder of this group is adrenoleukodystrophy (X-linked adrenoleukodystrophy or X-ALD). This is a rare, inherited disorder that leads to progressive damage to the brain and other tissues and eventually death. This disease can be considered both as neurodegenerative and neuroinflammatory.

X-ALD presents three main phenotypes: (i) an adult adrenomyeloneuropathy (AMN) with axonopathy in spinal cords, (ii) cerebral adrenomyeloneuropathy with brain demyelination (cAMN), and (iii) childhood variant (cALD) characterized by severe cerebral demyelination. X-ALD is the most frequently inherited leukodystrophy, with a minimum incidence of 1 in 17,000 including hemizygous males and carrier females.

Cerebrovascular diseases are a group of brain dysfunctions related to disease of the blood vessels supplying the brain. There are four types: stroke, transient ischaemic attack (TIA), subarachnoid haemorrhage and vascular dementia.

Epilepsy is an unpredictable, serious and potentially fatal disorder of the nervous system. About 50 million people worldwide have epilepsy.

Brain tumours are generated by an abnormal and uncontrolled cell division not only in the brain (neurons or glial cells) but also in blood vessels, cranial nerves, meninges, skull, and pituitary or pineal glands. Brain tumours also include those that have spread from primary cancer cells located in other organs (metastasis).

Nervous system viral diseases are caused by viral infections in the NS. These infections can induce neurological dysfunction and potentially serious inflammatory diseases such as encephalitis, an inflammation of the brain itself, meningitis that results in inflammation of the meninges or myelitis that means spinal cord inflammation. Rabies, measles, mumps, poliomyelitis, herpes simplex or varicella-zoster are types of nervous system viral infections.

Rare metabolic diseases (also known as Inborn Errors of Metabolism) are usually monogenic diseases where certain metabolic pathways are perturbed thus originating dysfunctions, in many cases on the central NS. They are chronically debilitating and life-threatening conditions.

Genetic mitochondrial diseases can be caused by mutations in either mtDNA or nDNA, that impair mitochondrial function and typically result in very severe multisystem disease from birth, including severe manifestations on the NS.

There is an urgent need for new treatments of central NS disorders.

A wide variety of deuterium enriched 2,4-thiazolidinediones have been described in US 2014/0275180. This document also discloses their prophetic use in the treatment of a variety of different diseases. However, this document fails to provide any evidence in this regard or regarding the ability of these compounds to cross the blood-brain barrier (BBB).

Pioglitazone is a drug marketed for use in the treatment of diabetes mellitus type 2. Pioglitazone is a potent agonist for peroxisome proliferator-activated receptor-gamma (PPARγ) and it has been proposed for the treatment of some neurodegenerative diseases including Alzheimer's, Parkinson's disease, ALS and Friedreich's ataxia. US2013/0274295 discloses the utility of Pioglitazone in the treatment of X-ALD based on pre-clinical data. Although pre-clinical models have shown promising results, clinical trials to date have failed to show clinical benefits in any of these extremely serious conditions.

In addition, Pioglitazone has been associated with unwanted side effects including cardiovascular effects, fluid retention, weight gain and bladder cancer. High doses of Pioglitazone are therefore undesirable as high systemic exposure would be likely to result in serious side effects.

Pioglitazone is a "dirty" drug which is converted to many metabolites in vivo. The metabolic pathway of Pioglitazone after oral administration has been studied in several animal species and in humans and the metabolites have been described in the literature (see e.g. Sohda et al, Chem. Pharm. Bull., 1995, 43(12), 2168-2172) and Maeshiba et al, Arzneim.-Forsch/Drug Res, 1997, 47 (I), 29-35). At least six metabolites have been identified, named M-I to M-VI. Amongst these metabolites, M-II, M-III and M-IV show some pharmacological activity but are less active than Pioglitazone in diabetic preclinical models.

The distribution of Pioglitazone and its metabolites in various tissues after oral administration of [$^{14}$C]-Pioglitazone to rats has also been studied (Maeshiba et al, Arzneim.-Forsch/Drug Res, 1997, 47 (1), 29-35). In most tissues the concentrations of Pioglitazone and metabolites M-I to M-VI were lower than that in plasma and one of the lowest concentrations of radioactivity was found in the brain where only Pioglitazone was mainly detected.

SUMMARY OF THE INVENTION

Surprisingly it has been found that central NS disorders can be treated by 5-[4-[2-(5-(1-hydroxyethyl)-2-pyridinyl) ethoxy]benzyl]-2,4-thiazolidinedione of formula (1), the M-IV metabolite of Pioglitazone.

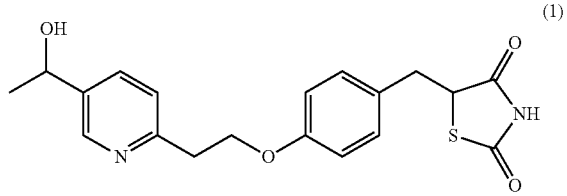 [SMILES: CC(O)c1ccc(CCOc2ccc(CC3SC(=O)NC3=O)cc2)nc1]

(1)

or a salt thereof.

The NS disorders include, but are not limited to, disorders in which the nervous system is affected during the entire progression of the diseases such as neurodegenerative diseases (e.g., Alzheimer's disease, Huntington's chorea, Parkinson's disease, amyotrophic lateral sclerosis (ALS), degenerative ataxias, multiple system atrophy and leukodystrophies), cerebrovascular diseases (e.g., global or local ischemia, intracerebral hemorrhage, stroke), seizures and epilepsy, viral diseases (e.g., meningitis, encephalitis), multiple sclerosis, brain tumors, and injury. NS disorders also include disorders in which the nervous system is only affected in the latest stages of the development of the condition and include rare metabolic diseases such as organic acidemias or fatty acid disorders and genetic mitochondrial disorders.

The invention is based at least in part on data showing the unexpected ability of the compound of formula (1) to cross the blood brain barrier. In addition, the compound of the invention has one or more desirable drug properties such as good oral bioavailability, low systemic plasma clearance, and a good volume of distribution. Furthermore, the compound of the invention is a reasonably "clean" drug, since in vivo it only converts to 5-(4-(2-(5-acetyl-2-pyridyl)ethoxy) benzyl)-2,4-thiazolidinedione (M-III metabolite of Pioglitazone) and both are excreted. Side effects due to unwanted metabolites are therefore minimised.

Thus, according to an aspect of the invention, there is provided a compound of formula (1) or pharmaceutically acceptable salts thereof or mixture of compounds of formula (1) for use as a medicament in particular for the treatment or prevention of central NS disorders. According to another aspect, the invention provides the use of a compound of formula (1) or pharmaceutically acceptable salts thereof or mixture of compounds of formula (1) for the manufacture of a medicament in particular for the treatment or prevention of central NS disorders. According to another aspect, the invention provides a method for the treatment or prevention of a disease of central NS comprising administering to a subject in need thereof an effective amount of a compound of formula (1) or pharmaceutically acceptable salts thereof or mixture of compounds of formula (1). According to another aspect of the invention there are provided pharmaceutical compositions comprising a compound of formula (1) or pharmaceutically acceptable salts thereof or mixtures of compounds of formula (1).

According to another aspect the present invention provides novel compounds (2) to (5):

(2) (R)-5-(4-(2-(5-((R)-1-hydroxyethyl)pyridine-2-yl) ethoxy)benzyl)thiazolidine-2,4-dione
(3) (R)-5-(4-(2-(5-((S)-1-hydroxyethyl)pyridine-2-yl) ethoxy)benzyl)thiazolidine-2,4-dione
(4) (S)-5-(4-(2-(5-((R)-1-hydroxyethyl)pyridine-2-yl) ethoxy)benzyl)thiazolidine-2,4-dione
(5) (S)-5-(4-(2-(5-((S)-1-hydroxyethyl)pyridine-2-yl) ethoxy)benzyl)thiazolidine-2,4-dione
or a pharmaceutically acceptable salt thereof According to still another aspect the present invention provides mixtures of one or more of the compounds (2) to (5) or pharmaceutically acceptable salts thereof for use in the treatment or prevention of central nervous system disorders. According to another aspect, the invention provides the use of one or more of the compounds (2) to (5) or pharmaceutically acceptable salts thereof for the manufacture of a medicament for the treatment or prevention of central NS disorders. According to another aspect, the invention provides a method for the treatment or prevention of a disease of central NS comprising administering to a subject in need thereof an effective amount of one or more of the compounds (2) to (5) or pharmaceutically acceptable salts thereof.

In yet another aspect the invention provides pharmaceutical compositions comprising a one or more compounds of formulae (2) to (5) or pharmaceutically acceptable salts thereof, including mixtures of compounds of formula (2) to (5) for use in the treatment or prevention of central NS disorders.

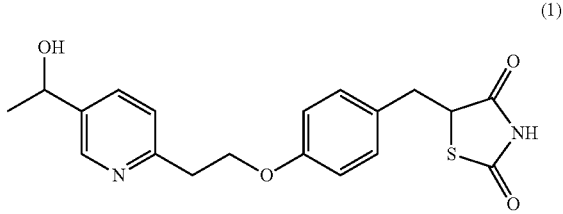 [SMILES: CC(O)c1ccc(CCOc2ccc(CC3SC(=O)NC3=O)cc2)nc1]

(1)

In another aspect, the invention provides a method for treating or preventing central nervous system disorders, including neurodegenerative diseases (such as Alzheimer's disease, Huntington's chorea, Parkinson's disease, amyotrophic lateral sclerosis (ALS), degenerative ataxias, multiple system atrophy, multiple sclerosis and leukodystrophies such as ALD), cerebrovascular diseases, seizures, epilepsy, viral diseases, brain tumours, neuroinflammatory diseases NS disorders that affect the nervous system in the latest stages of the development of the condition including rare metabolic diseases such as organic acidemias or fatty acid disorders and genetic mitochondrial disorders through the administration of a compound of formula (1) or a pharmaceutically acceptable salt thereof, or of one or more compounds of formulae (2) to (5) or pharmaceutically acceptable salts thereof.

DESCRIPTION OF THE PREFERRED EMBODIMENTS

Figure 1:
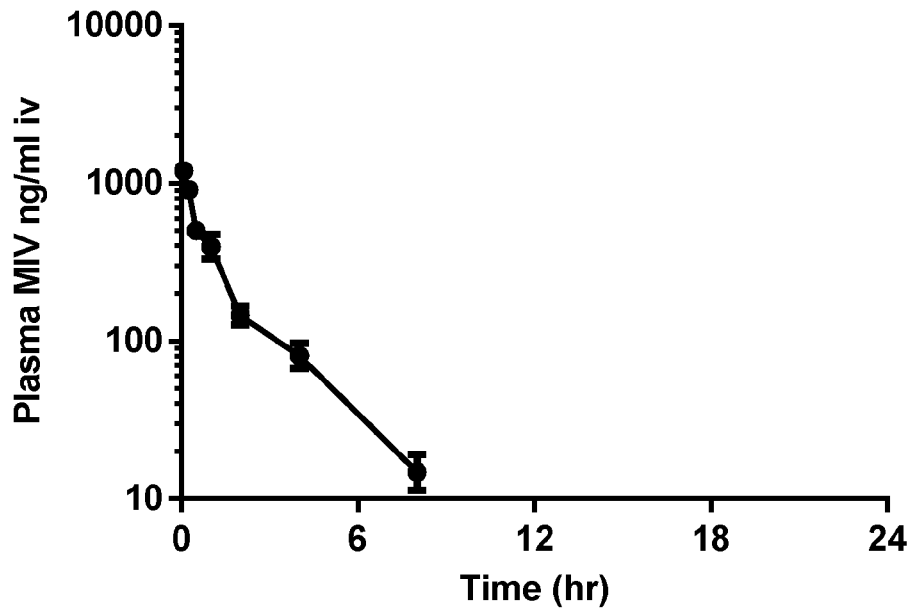
FIG. 1 represents the concentration of compound of formula (1) in plasma of a C57BL/6 mouse after a single intravenous administration of 1 mg/Kg of said compound.

In the present invention the terms "compound of formula (1)", "M-IV", "MIV" and "M4" indistinctively refer to 5-[4-[2-(5-(1-hydroxyethyl)-2-pyridinyl)ethoxy]benzyl]-2,4-thiazolidinedione, which has the structure depicted above.

In one aspect, administration of compound of formula (1), or a pharmaceutically acceptable salt is useful for the treatment or prevention of central NS disorders such as neurodegenerative diseases (e.g., Alzheimer's disease, Huntington's chorea, Parkinson's disease, amyotrophic lateral sclerosis (ALS), degenerative ataxias, multiple system atrophy, multiple sclerosis (MS) and leukodystrophies, such as adrenoleukodistrophy (ALD or X-ALD), cerebrovascular diseases (e.g., global or local ischemia, intracerebral hemorrhage, stroke), seizures and epilepsy, viral diseases (e.g., meningitis, encephalitis), brain tumors and neuroinflammatory diseases. NS disorders also include disorders in which the nervous system is only affected in the latest stages of the development of the disorder. These disorders comprise rare metabolic diseases such as organic acidemias or fatty acid disorders and genetic mitochondrial disorders.

The term "treatment" or "to treat" in the context of this specification means to ameliorate or eliminate the disease or one or more symptoms associated with said disease. "Treatment" also encompasses ameliorating or eliminating the physiological sequelae of the disease.

The term "ameliorate" in the context of this invention is understood as meaning any improvement on the situation of the patient treated.

The term "prevention" or "to prevent" refer to the reduction in the risk of acquiring or developing a given disease or disorder, or the reduction or inhibition of the recurrence or a disease or disorder.

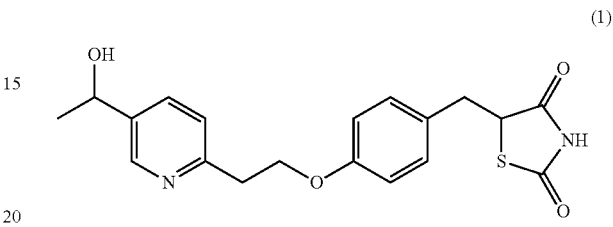

(1)

The compound of formula (1) can be named 5-(4-(2-(5-(1-hydroxyethyl)pyridine-2-yl)ethoxy)benzyl)thiazolidine-2,4-dione and has two chiral centres. One of them is the carbon atom in the 5-position of the thiazolidine-dione ring and the other asymmetric atom is at position 1 of the hydroxyethyl group as shown by the arrows:

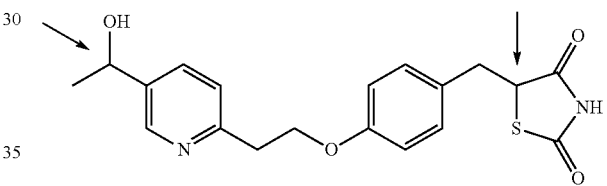

As used herein the term "compound of formula (1)" is used to designate all possible stereoisomers, including enantiomers and diastereomers, and mixtures including racemic mixtures thereof.

In another aspect, the invention provides novel compounds (2) to (5):

(2)  (R)-5-(4-(2-(5-((R)-1-hydroxyethyl)pyridine-2-yl)ethoxy)benzyl)thiazolidine-2,4-dione

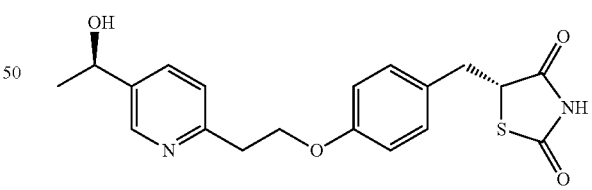

(3)  (R)-5-(4-(2-(5-((S)-1-hydroxyethyl)pyridine-2-yl)ethoxy)benzyl)thiazolidine-2,4-dione

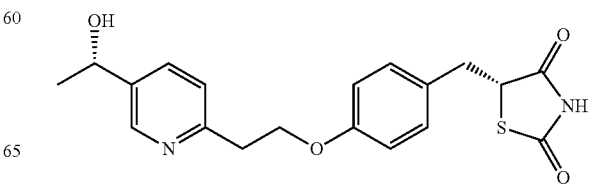

(4) (S)-5-(4-(2-(5-((R)-1-hydroxyethyl)pyridine-2-yl)ethoxy)benzyl)thiazolidine-2,4-dione

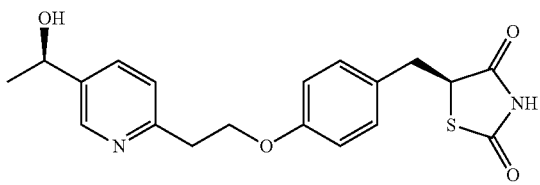 [SMILES: C[C@@H](O)c1ccc(CCOc2ccc(C[C@@H]3SC(=O)NC3=O)cc2)nc1]

(5) (S)-5-(4-(2-(5-((S)-1-hydroxyethyl)pyridine-2-yl)ethoxy)benzyl)thiazolidine-2,4-dione

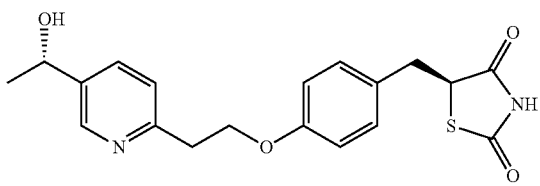 [SMILES: C[C@H](O)c1ccc(CCOc2ccc(C[C@@H]3SC(=O)NC3=O)cc2)nc1]

or pharmaceutically acceptable salts thereof.

Although compounds (2) to (5) have been prepared and isolated their absolute (R/S) configuration has not yet been determined and only their optical rotation has been determined.

Preferably, reference to compounds (1) to (5) in the present invention is intended to designate compounds (1) to (5) having hydrogen atoms which are predominantly in the form of its isotope $^1$H, i.e. no more than 1% of the total number of hydrogen atoms per mole of compound are in the form of the $^2$H isotope (deuterium), still more preferably no more than 0.015% (which is the natural abundance of deuterium) of the total number of hydrogen atoms per mole of compound are in the form of the $^2$H isotope (deuterium).

In a particular embodiment the following mixtures of compound (2) to (5) are preferred:
  (a) Mixtures comprising compounds (2) and (3), preferably being compounds (2) and (3) the only compounds of formula (1) present in the mixtures;
  (b) Mixtures comprising (4) and (5), preferably being compounds (4) and (5) the only compounds of formula (1) present in the mixtures;
  (c) Mixtures comprising (2) and (4), preferably being compounds (2) and (4) the only compounds of formula (1) present in the mixtures; and
  (d) Mixtures comprising (3) and (5), preferably being compounds (3) and (5) the only compounds of formula (1) present in the mixtures.

Mixtures (c) and (d) are particularly preferred.

In the mixtures (a) to (d) mentioned above, it is particularly preferred that the two compounds mentioned in each one of the mixtures are present in equimolar quantities. Said mixtures may compound also minor amounts (preferably less than 10 wt. %, more preferably less than 3 wt %, still more preferably less than 1 wt. % and most preferably less than 0.1 wt. % of other compounds of formula (1).

Another aspect of the invention provides compounds (2) to (5) or a pharmaceutically acceptable salt thereof or mixtures (a) to (d) or pharmaceutically acceptable salts thereof for use as medicaments. The compounds of the invention can be used to treat diseases such as central nervous system disorders amongst others.

For use in the treatment of central NS disorders several factors may be considered when selecting a preferred compound. A compound showing high brain-to-plasma exposure is preferred. A preferred compound displays potent PPAR-gamma agonist activity but compounds with less potent PPAR-gamma agonist activity are also useful. Other factors, including but not limited to, pharmacological activity (other than PPAR-gamma), ADME, pharmacokinetic profile, toxicity, safety, brain distribution properties, compound accumulation in tissues, compound metabolism and clearance, genotypic variation in clearance and physicochemical properties may also be considered for the selection of a preferred compound. A preferred compound has low central nervous system toxicity. A preferred compound has low systemic toxicity. The presence or absence of PPAR alpha activity may also be considered. In some cases it is desirable for the compound to result in low or no accumulation in the brain. This can reduce the risk of central nervous system toxicity and/or allow rapid reversal of drug effect in the central nervous system. In other cases, high brain accumulation with limited systemic exposure may be preferred. This can result in greater central nervous system exposure to the drug and higher efficacy. It is often advantageous for the compound not to be the subject to significant genotypic variations in clearance. This results in more consistent efficacy. These activities may be determined by use of the appropriate in vitro and in vivo assays.

In another aspect, the invention provides a method for treating or preventing central NS disorders, including neurodegenerative diseases, cerebrovascular diseases, seizures, epilepsy, viral diseases, brain tumours and neuroinflammatory diseases. The aspect also includes a method for treating or preventing central NS disorders in which the nervous system is only affected in the latest stages of the development of the disorder include rare metabolic diseases such as organic acidemias or fatty acid disorders and genetic mitochondrial disorders by the administration of a compound of formula (2) to (5) or a pharmaceutically acceptable salt thereof or by administration of a mixture of one or more compounds of formulae (2) to (5).

Another aspect of the present invention relates to the use of a compound of formula (1) or a pharmaceutically acceptable salt thereof, or of one or more compounds of formula (2) to (5) or pharmaceutically acceptable salts thereof, or mixtures (a) to (d) or pharmaceutically acceptable salts thereof, for the manufacture of a medicament for the treatment or prevention of central NS disorders, including neurodegenerative diseases, cerebrovascular diseases, seizures, epilepsy, viral diseases, brain tumours and neuroinflammatory diseases. The aspect also includes the use of a compound of formula (1) or a pharmaceutically acceptable salt thereof, or of one or more compounds of formula (2) to (5) or pharmaceutically acceptable salts thereof, or mixtures (a) to (d) or pharmaceutically acceptable salts thereof, for the manufacture of a medicament for the treatment or prevention of central NS disorders in which the nervous system is only affected in the latest stages of the development of the disorder include rare metabolic diseases such as organic acidemias or fatty acid disorders and genetic mitochondrial disorders.

Another aspect of the present invention relates a compound of formula (1) or a pharmaceutically acceptable salt thereof, or of one or more compounds of formula (2) to (5) or pharmaceutically acceptable salts thereof, or mixtures (a) to (d) or pharmaceutically acceptable salts thereof, for use in the treatment or prevention of central NS disorders, including neurodegenerative diseases, cerebrovascular diseases, seizures, epilepsy, viral diseases, brain tumours and neuroinflammatory diseases. The aspect also includes a compound of formula (1) or a pharmaceutically acceptable salt thereof, or of one or more compounds of formula (2) to (5) or pharmaceutically acceptable salts thereof, or mixtures (a) to (d) or pharmaceutically acceptable salts thereof, for use in the treatment or prevention of central NS disorders in which the nervous system is only affected in the latest stages of the development of the disorder include rare metabolic diseases such as organic acidemias or fatty acid disorders and genetic mitochondrial disorders.

In particular embodiments of the aspects of the invention described above, the disorder is selected from the group consisting of neurodegenerative diseases, cerebrovascular diseases, seizures, epilepsy, viral diseases and brain tumours more preferably the disorder is a neurodegenerative disease; more preferably the disorder is selected from the group consisting of Alzheimer's disease, Huntington's chorea, Parkinson's disease, Friedreich's ataxia, ALS multiple sclerosis, and X-ALD; more preferably the disorder is selected from the group consisting of Alzheimer's disease, Huntington's chorea, Parkinson's disease or multiple sclerosis; more preferably the disorder is multiple sclerosis; more preferably the disorder is a leukodystrophy such as adrenoleukodystrophy (ALD or X-ALD).

In other particular embodiments of the aspects of the invention described above, the disorder is a cerebrovascular disease.

A preferred compound or mixture of compounds may be selected for a particular route of delivery. Some compounds or mixture of compounds may also be preferred based on their use to treat a particular disease.

The compounds of the invention can be in the form of a pharmaceutically acceptable salt. The term "pharmaceutically acceptable salt" refers to salts prepared from pharmaceutically acceptable inorganic and organic acids.

Illustrative pharmaceutically acceptable acid addition salts of the compounds of the present invention can be prepared from the following acids, including without limitation, formic, acetic, propionic, benzoic, acetic, propionic, benzoic, succinic, glycolic, gluconic, lactic, maleic, malic, tartaric, citric, nitric, ascorbic, glucuronic, maleic, fumaric, pyruvic, aspartic, glutamic, benzoic, hydrochloric, hydrobromic, hydroiodic, isocitric, xinafoic, tartaric, trifluoroacetic, pamoic, propionic, anthranilic, mesylic, napadisylate, oxalacetic, oleic, stearic, salicylic, p-hydroxybenzoic, nicotinic, phenylacetic, mandelic, embonic (pamoic), methanesulfonic, phosphoric, phosphonic, ethanesulfonic, benzenesulfonic, pantothenic, toluenesulfonic, 2-hydroxyethanesulfonic, sulfanilic, sulfuric, salicylic, cyclohexylaminosulfonic, algenic, β-hydroxybutyric, galactaric and galacturonic acids. Exemplary pharmaceutically acceptable salts include the salts of hydrochloric acid and hydrobromic acid.

The utility of the compound of formula (1), including stereoisomers (2) to (5), mixtures (a) to (d) and pharmaceutically acceptable salt thereof can be demonstrated in appropriate in vitro or in vivo assays as described in the examples.

The compounds of the invention or pharmaceutically acceptable salts may be used according to the invention when the patient is also administered or in combination with one or more of another therapeutic agent selected from antiinflammatory and analgesic agents, dopamine agonists (e.g. levodopa), MAO-B inhibitors, catechol O-methyltransferase (COMT) inhibitors, anticholinergics, other antiparkinsonians (e.g. amantadine), antiNMDA receptors (e.g. memantine), cholinesterase inhibitors, ACE inhibitors, glutamate antagonist (e.g. riluzole), antioxidants, immunomodulators (e.g. fingolimod, anti CD52, CD25 and CD20 monoclonal antibodies, interferon-β-1a, natalizumab, laquinimod, dimethylfumarate) chemotherapeutics, enzyme replacement therapy agents, substrate reduction therapy agents, corticosteroids, antiproliferatives (e.g. methotrexate), anticonvulsant medications, anticoagulants, antihypertensives and neuroprotectives. The compounds of the invention may also be used when the patient is undergoing gene therapy, bone marrow transplantation, deep brain stimulation or radiotherapy.

Pharmaceutical compositions comprising compounds (2) to (5), mixtures (a) to (d) or a pharmaceutically acceptable salt represent another aspect of the invention. Any suitable route of administration can be used. For example, any of oral, intraoral, topical, epicutaneous, subcutaneous, transdermal, intramuscular, parenteral, ocular, rectal, vaginal, inhalation, buccal, sublingual and intranasal delivery routes may be suitable. Oral administration may be preferred. Oral forms of pharmaceutical compositions may be solid or liquid. Suitable dosage forms may be tablets, capsules, pills, granules, suspensions, emulsions, syrups or solutions. Preferably the pharmaceutical composition is a solid form selected from the group consisting of tablets, capsules, pills or granules. Particularly preferred are tablets. Oral solutions or suspensions are also preferred. These are advantageous when the patient has difficulty swallowing, for example as a result of the disease or for geriatric and paediatric use. Sublingual preparations are also advantageous.

By an "effective" amount or a "therapeutically effective amount" of a drug or pharmacologically active agent is meant a nontoxic but sufficient amount of the drug or agent to provide the desired effect. The amount that is "effective" will vary from subject to subject, depending on the age and general condition of the individual, the particular active agent or agents, and the like. Thus, it is not always possible to specify an exact "effective amount". However, an appropriate "effective" amount in any individual case may be determined by one of ordinary skill in the art using routine experimentation. Thus, the dose of the active agent will depend on the nature and degree of the condition, the age and condition of the patient, and other factors known to those skilled in the art. A typical daily dosage is from 0.1 to 200 mg, preferably from 20 to 200 mg, e.g. for an adult 10-100 mg given as a single dose with no further dosing or in multiple doses, for example one to three times per day. The compounds described herein may also be administered in daily doses of from 80 to 600 mg.

The pharmaceutical compositions may contain conventional excipients known in the art and may be prepared by conventional methods.

The pharmaceutical compositions may further comprise one or more therapeutic agent. Combination treatments may be administered simultaneously, sequentially or separately, by the same or by different routes, or before, during and after surgical or intervention procedures.

The compounds of the invention may be prepared by any suitable method known in the art and/or by the processes described below. It will also be appreciated that functional groups, such as amino or hydroxyl groups, present in the various compounds described, and which it is desired to retain, may need to be in protected form before any reaction is initiated. In such instances, removal of the protecting group may be the final step in a particular reaction. Suitable protecting groups for such functionality will be apparent to those skilled in the art. For specific details see "Protective Groups in Organic Synthesis", Wiley Interscience, T W Greene, PGM Wuts. Any mixtures of final products or intermediates obtained can be separated on the basis of the physico-chemical differences of the constituents, in known manner, into the pure final products or intermediates, for example by chromatography, distillation, fractional crystallization, or by formation of a salt if appropriate or possible under the circumstances.

The compounds according to the invention may be prepared by the following or similar processes.

Compound 5-[4-[2-(5-(1-hydroxyethyl)-2-pyridinyl) ethoxy]benzyl]-2,4-thiazolidinedione of formula (1) can be prepared according to Scheme 1 (see e.g. *J. Med. Chem.* 1996, 39(26), 5053).

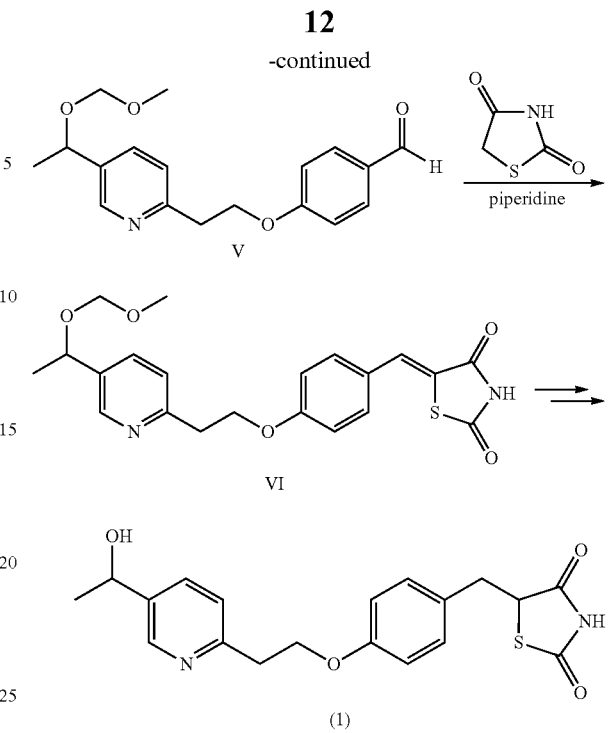

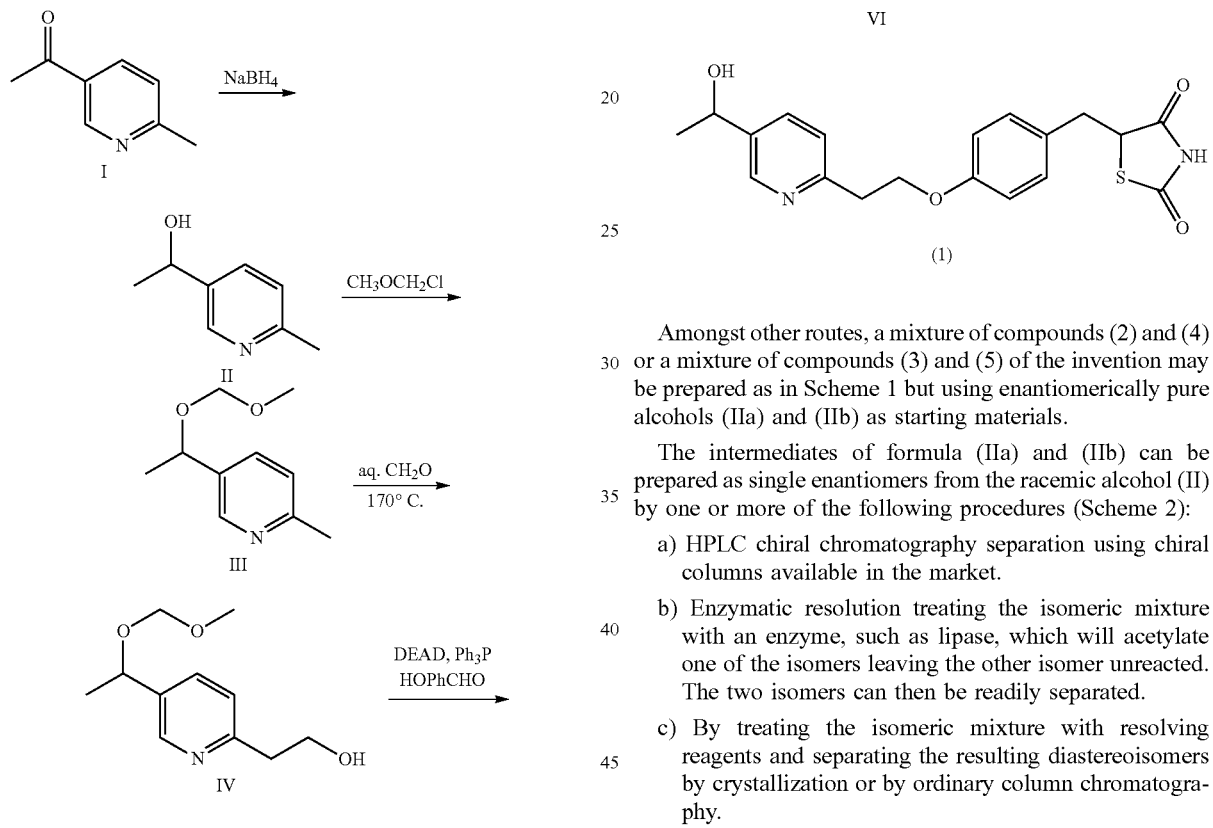

Amongst other routes, a mixture of compounds (2) and (4) or a mixture of compounds (3) and (5) of the invention may be prepared as in Scheme 1 but using enantiomerically pure alcohols (IIa) and (IIb) as starting materials.

The intermediates of formula (IIa) and (IIb) can be prepared as single enantiomers from the racemic alcohol (II) by one or more of the following procedures (Scheme 2):

a) HPLC chiral chromatography separation using chiral columns available in the market.

b) Enzymatic resolution treating the isomeric mixture with an enzyme, such as lipase, which will acetylate one of the isomers leaving the other isomer unreacted. The two isomers can then be readily separated.

c) By treating the isomeric mixture with resolving reagents and separating the resulting diastereoisomers by crystallization or by ordinary column chromatography.

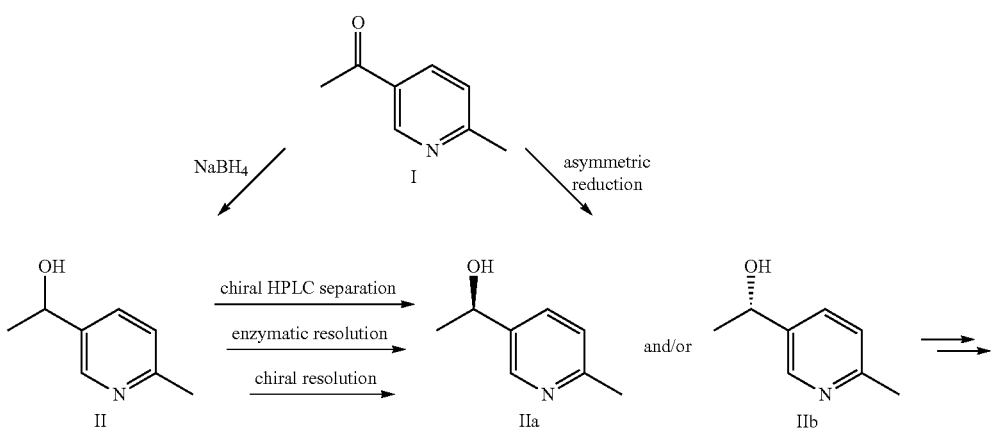

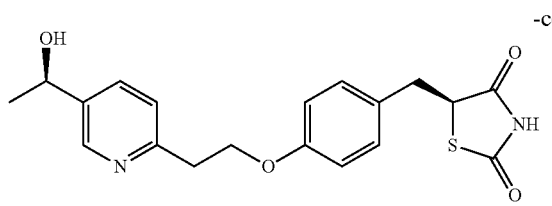

(4)

+

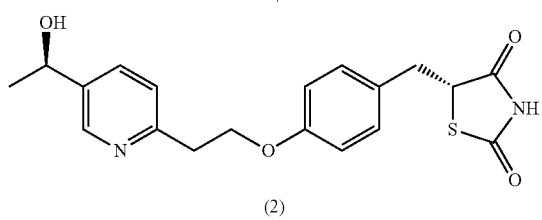

(2)

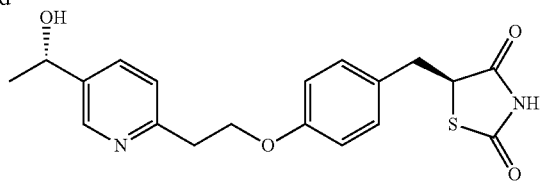

(5)

+

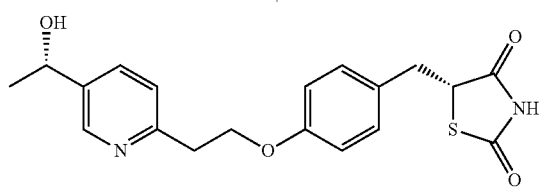

(3)

and/or

An alternative method to prepare intermediates (IIa) and (IIb) as single enantiomers by chiral synthesis, treating a substrate of formula (I) with an appropriate chiral reducing agent known to those skilled in the art.

Yet another method to prepare mixtures (c)—comprising compound (2) and (4)—and (d)—comprising compounds (3) and (5)—(scheme 3), includes the resolution of the racemic mixture VIII using the already described methods (chiral HPLC separation, enzymatic resolution, chiral resolution, etc) followed by double bond reduction in each of the enantiomers VIIIa and VIIIb.

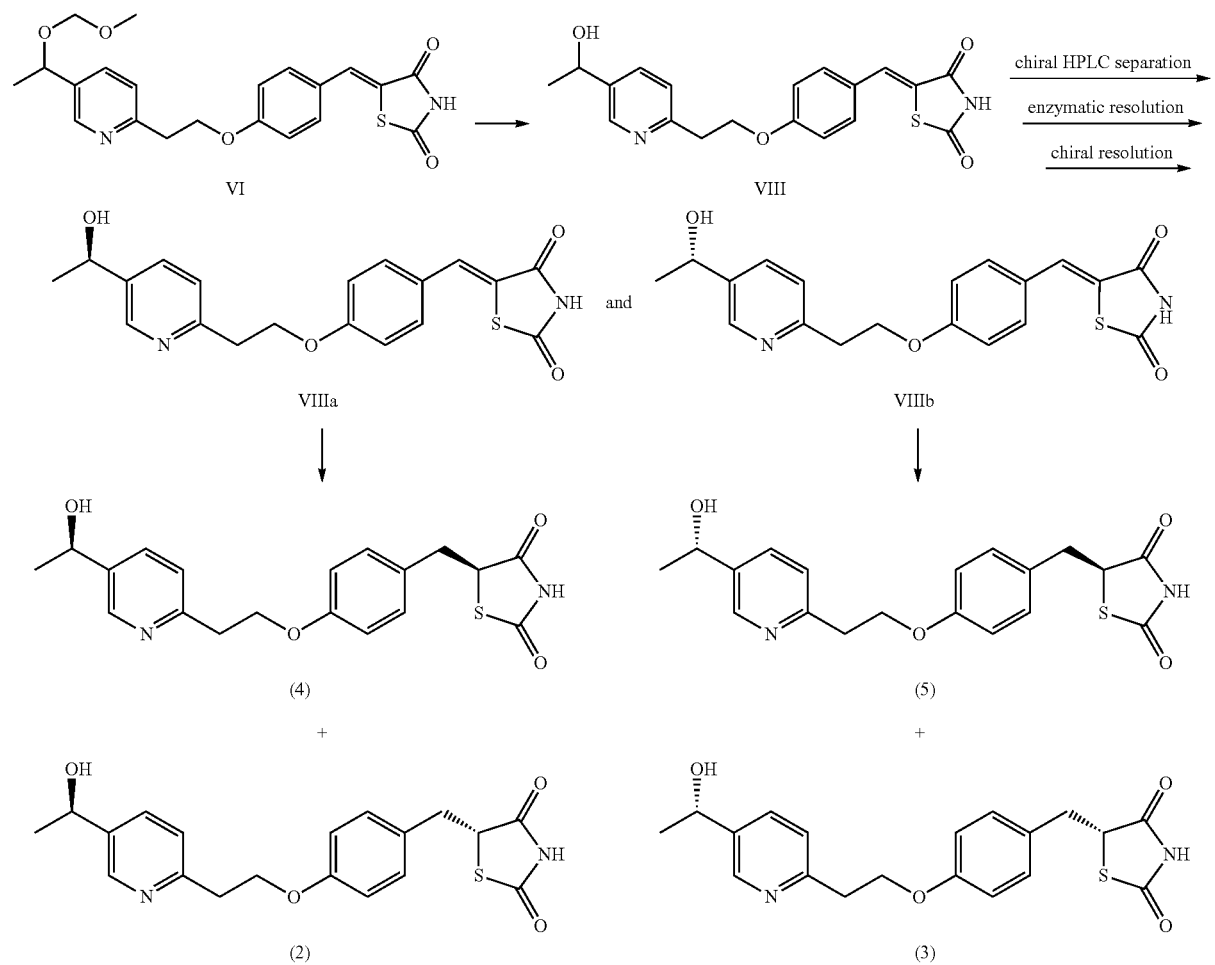

Scheme 3

Mixture (b) (comprising compounds of formula (4) and (5)) and mixture (a) (comprising compounds of formula (2) and (3)) of the invention may be prepared by asymmetric hydrogenolysis of a compound of formula VI using for example Rhodium or Iridium catalysts in the presence of chiral ligands as shown on Scheme 4. Chiral reduction of the double bond may also be performed using biocatalysts (e.g. *Rhodotorula rubra* and *Rhodotorula glutinis*).

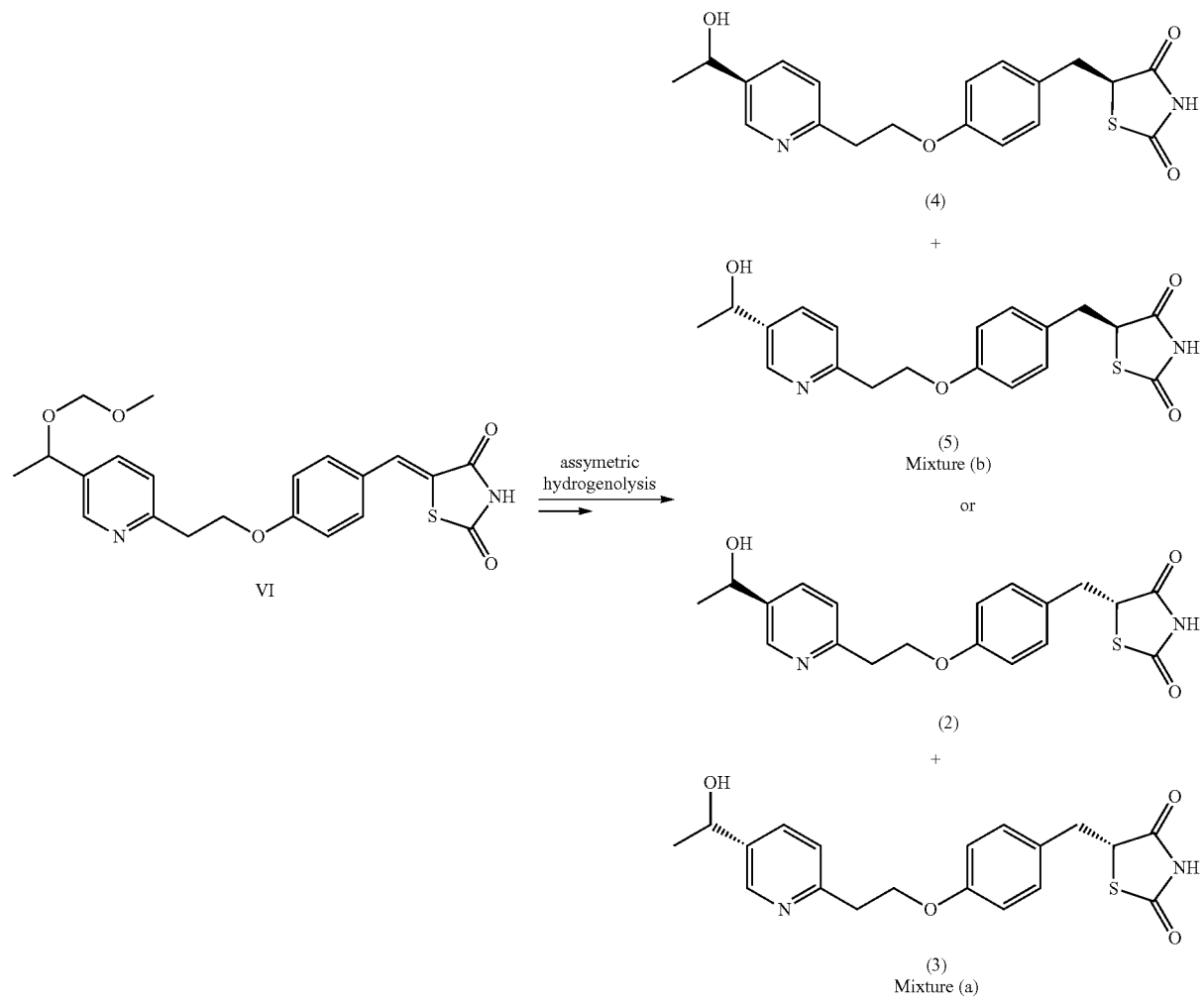

Scheme 4

Compounds of formula (2), (3), (4) and (5) may be obtained from mixtures (c) and (d) (Scheme 45) by chiral HPLC separation. Alternatively, the desired enantiomerically pure compounds can be prepared by chiral synthetic procedures known to those skilled in the art (for example: asymmetric hydrogenolysis of the corresponding single isomer of compound VI).

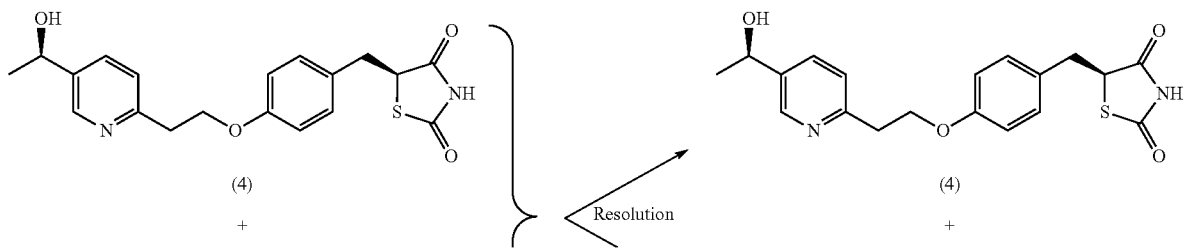

Scheme 5

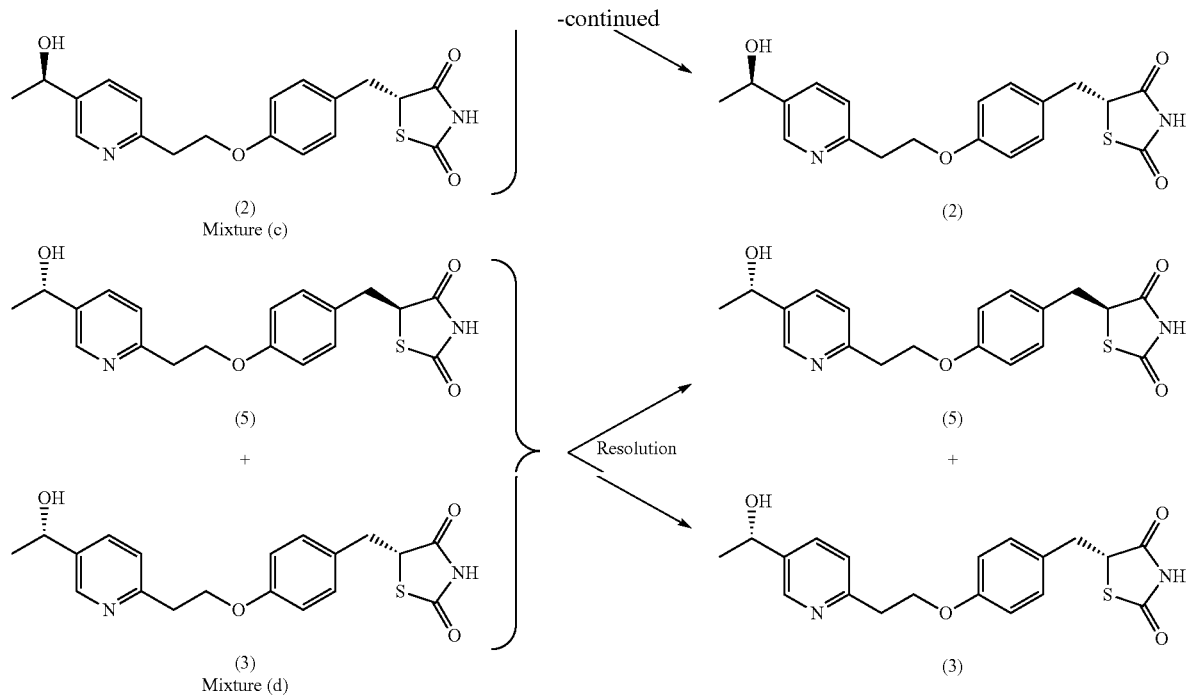

Abbreviations:
ACE: Angiotensin-converting enzyme
ADME: Absorption, distribution, metabolism and excretion
ALS: Amyotrophic lateral sclerosis
AMN: Adrenomyeloneuropathy
AUC: Area under the curve
C57BL/6 mouse: C57 black 6 mouse
cALD: cerebral variant of ALD
cAMN: Cerebral adrenomyeloneuropathy
CD20: B-lymphocyte antigen CD20
CD25: the alpha chain of the IL-2 receptor
CD52: Cluster of differentiation 52
cDNA: Complementary deoxyribonucleic acid
Cmax: Peak plasma concentration after administration.
COMT: Catechol O-methyltransferase
DEAD: Diethyl azodicarboxylate
$EC_{50}$: Half maximal effective concentration
hERG: human Ether-a-go-go-Related Gene
HPLC: High performance liquid chromatography
LLOQ: Lower limit of quantification
MAO-B: Monoamine oxidase B
mtDNA: mitochondrial deoxyribonucleic acid
NMDA: N-Methyl-D-aspartic acid
nDNA: nuclear deoxyribonucleic acid
NS: Nervous system
Ph: phenyl
PPARγ: Peroxisome proliferator-activated receptor-gamma
qPCR: Quantitative polymerase chain reaction
TIA: Transient ischaemic attack
Tmax: Time to reach Cmax
VSS: Apparent volume of distribution at steady state
X-ALD: X-linked adrenoleukodystrophy The following examples support the invention.

Example 1: Pharmacokinetic Profile and Brain Distribution

Protocol: Pharmacokinetic parameters and brain distribution of 5-(4-(2-(5-(1-hydroxyethyl)pyridine-2-yl)ethoxy)benzyl)thiazolidine-2,4-dione (racemate or stereoisomers) following single oral (4.5 mg/kg) and intravenous (1 mg/kg) dose administration to male C57 BL/6 mice were determined. Blood samples and brain samples were collected pre-dosing and different times post dosing for both oral and i.v pharmacokinetics. All samples were processed for analysis by protein precipitation using acetonitrile and analyzed with fit-for-purpose LC/MS/MS method. The lower limit of quantification (LLOQ) in plasma and brain for 5-(4-(2-(5-(1-hydroxyethyl)pyridine-2-yl)ethoxy)benzyl)thiazolidine-2,4-dione (1) is 0.99 ng/mL. Pharmacokinetic parameters were calculated using the non-compartmental analysis tool of Phoenix WinNonlin.

Figure 2:
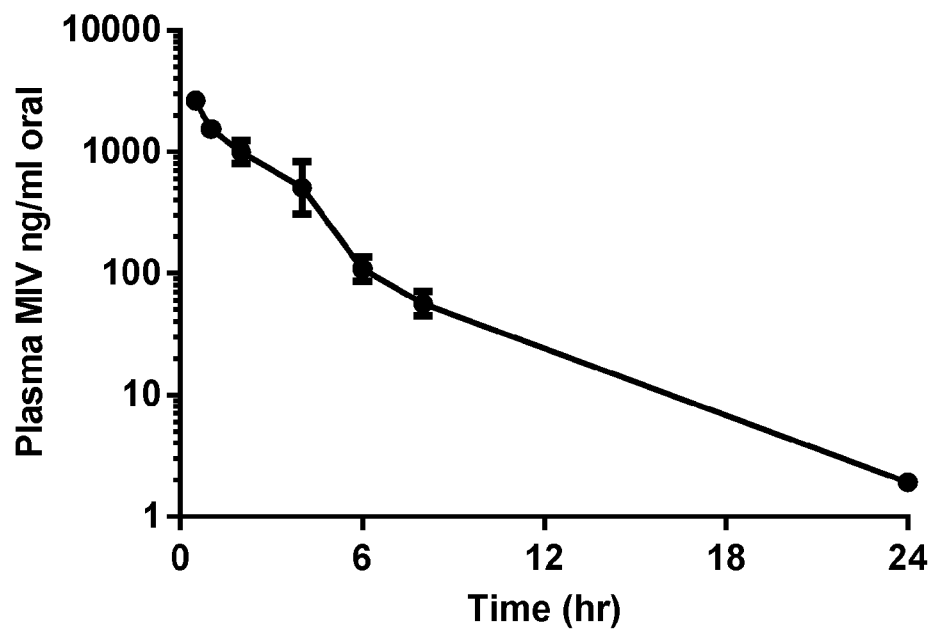
FIG. 2 represents the concentrations of compound of formula (1) in plasma of a C57BL/6 mouse after a single oral administration of 4.5 mg/Kg of said compound.
Figure 3:
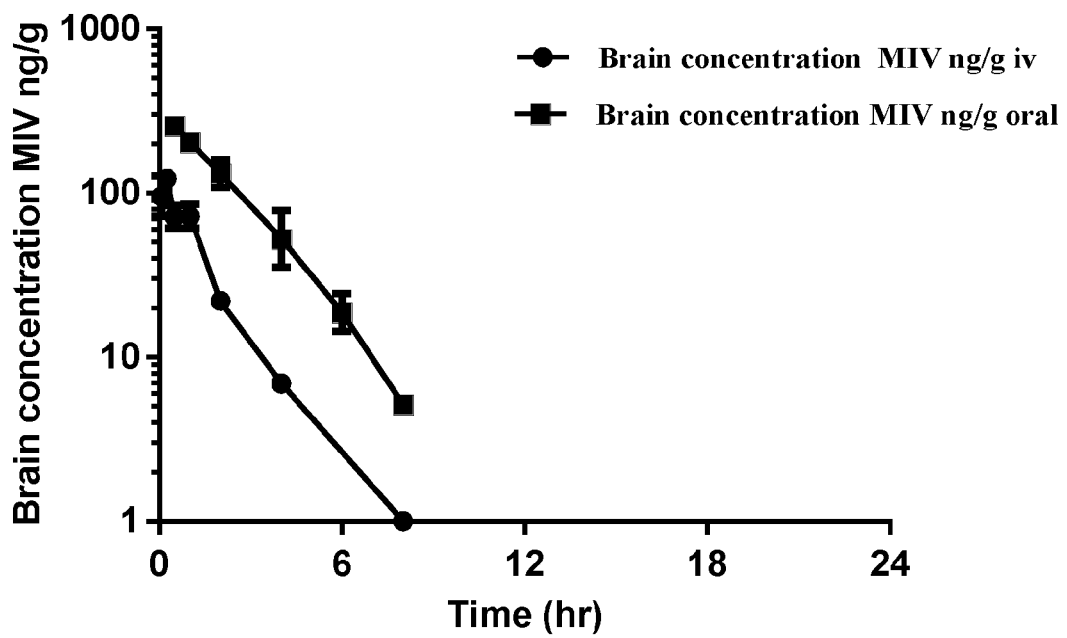
FIG. 3 represents the concentration of compound of formula (1) in brain tissue of a C57BL/6 mouse after a single oral administration of 4.5 mg/Kg of said compound (line with circle markers) and after a single intravenous administration of 1 mg/Kg of said compound (line with square markers).

The results from these experiments are shown in FIG. 1, FIG. 2 and FIG. 3. The data clearly demonstrates that 5-(4-(2-(5-(1-hydroxyethyl)pyridine-2-yl)ethoxy)benzyl)-thiazolidine-2,4-dione (1) exhibits a good pharmacokinetic profile, low systemic plasma clearance and acceptable Volume of Distribution (Vss) with a brain-plasma ratio exposure of 0.12.

Following a single intravenous administration of racemic 5-(4-(2-(5-(1-hydroxyethyl)pyridine-2-yl)ethoxy)benzyl) thiazolidine-2,4-dione (FIG. 1) to C57BL/6 mice at 1 mg/kg dose, the compound exhibited low systemic plasma clearance (11.79 mL/min/kg, normal liver blood flow in mice=90 mL/min/kg) with terminal elimination plasma half-life of 1.79 hr. The Vss was 2-fold higher than the normal volume of total body water (0.7 L/kg).

After a single oral administration of racemic 5-(4-(2-(5-(1-hydroxyethyl)pyridine-2-yl)ethoxy)benzyl)thiazolidine-2,4-dione (1) to C57BL/6 mice at 4.5 mg/kg dose (FIG. 2), plasma concentrations were observed until 24 hr (1 animal). The Tmax in plasma was 0.50 hr. The oral bioavailability was 85%.

FIG. 3 shows that brain concentrations for both intravenous and oral pharmacokinetic profiles were observed until 8 hr. Tmax in brain is 0.50 hr with brain-to-plasma exposure (AUClast) ratio of 0.12.

These results indicate that 5-(4-(2-(5-(1-hydroxyethyl) pyridine-2-yl)ethoxy) benzyl)thiazolidine-2,4-dione has a favourable pharmacokinetic profile including good oral bioavailability and a brain-to-plasma exposure ratio of 0.12, thus the compound meaningfully crosses the blood brain barrier.

Example 2: Mechanism of Action: In Vitro Pharmacology

Protocol: To determine the mechanism of action through the agonism of PPAR gamma, a cellular functional assay was performed using a human recombinant cell line cotransfected with a PPRE luciferase reporter, PPAR-γ, RXR-α and coactivator DRIP205.

Transfected cells were treated with increasing doses of compounds. Luciferase activity was detected by alphascreen technology and normalized based on β-galactosidase activity. The results are expressed as the fold induction over the control (Rosiglitazone 10 μM). Dose response curves were obtained. Results were calculated as $EC_{50}$ that is the concentration of compound that provokes 50% control agonist response.

$EC_{50}$ racemic 5-(4-(2-(5-(1-hydroxyethyl)pyridine-2-yl) ethoxy)benzyl)thiazolidine-2,4-dione=9.3 μM The results from these experiments indicate that racemic 5-(4-(2-(5-(1-hydroxyethyl)pyridine-2-yl)ethoxy)benzyl) thiazolidine-2,4-dione and its stereoisomers have varying PPAR gamma agonists activities, with a range of $EC_{50}$s. These data show that these compounds activate PPAR gamma receptors and consequently the biological functions depending on this activation.

Example 3

General Experimental Conditions $^1$H spectra were recorded on 400 MHz Varian NMR spectrometer using appropriate deuterated solvents. Chromatographic analyses of the compounds were conducted using appropriate methods as shown below.

LCMS Method

Column: Agilent Zorbax 3.5 μm, SB-C8 (4.6×75 mm); wavelength: 210 nm; flow: 1 mL/min; run time: 7 min; mobile phase-gradient (t/% B): 0/30, 3.5/95, 5/95, 5.5/30, 7/30 [A: Water (0.1% formic acid); B: Acetonitrile]; MASS: Agilent-single quad-multimode-APCI-ESI.

Chiral HPLC Method

Column: Chiralpak-IA 5 μm (4.6 mm×250 mm); wavelength: 210 nm; flow: 0.7 mL/min; run time: 30 min; mobile phase-isocratic: 65/35 (A/B) [A: n-Hexane (0.05% triethylamine and 0.1% trifluroacetic acid), B: Isopropyl alcohol].

Chiral Prep-HPLC Method

Column: Chiralpak-IA 5 Lm (250×20 mm); wavelength: 254 nm; flow: 18 ml/min; run time: 60 min; mobile phase-isocratic 50/50 (A/B): A: n-Hexane, B: EtOH (0.05% triethylamine).

HPLC Method

Column: Symmetry Shield RP-18, 5 μm (4.6×250 mm); wavelength: 210 nm; flow: 1 mL/min; run time: 28 min; mobile phase-gradient: (t/% B): 0/10, 8/10, 12/60, 16/80, 20/80, 24/10, 28/10 [A: Water (potassium dihydrogen o-phosphate (pH~3)), B: Acetonitrile]

Example 4: 5-(4-(2-(5-(1-hydroxyethyl)pyridin-2-yl) ethoxy)benzyl)thiazolidine-2,4-dione (1) was Prepared According to Scheme 6

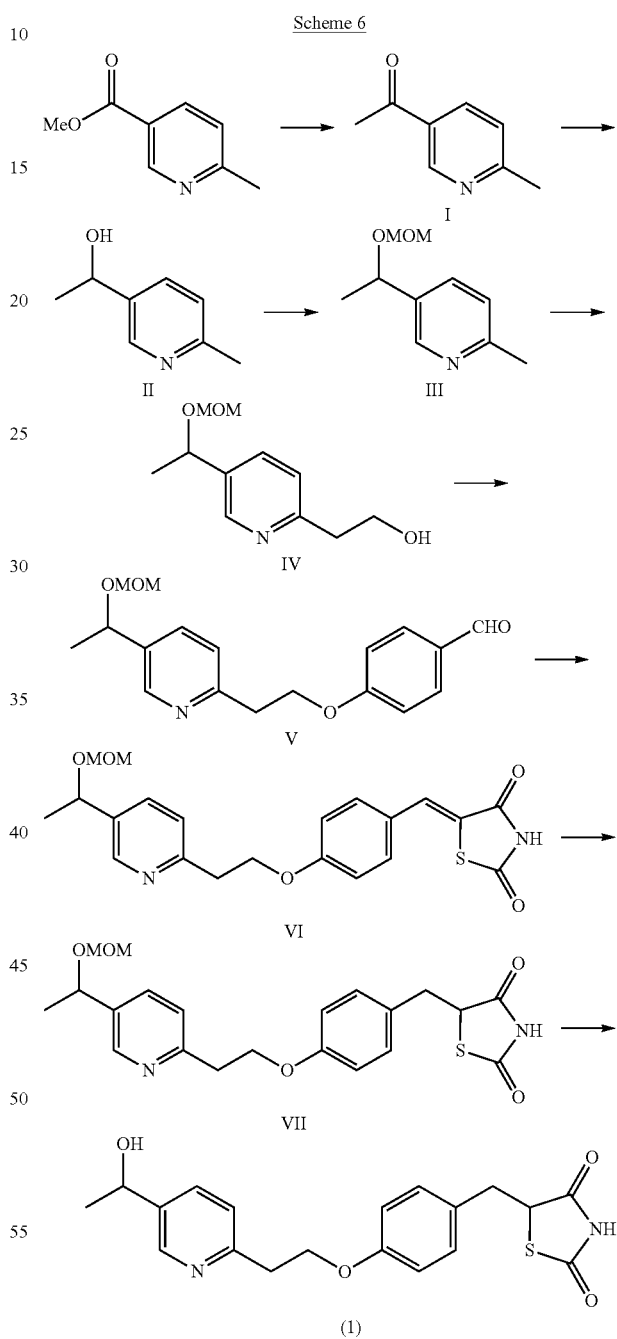

1-(6-methyl-pyridin-3-yl)-ethanol (II)

LiHMDS (1.0 M in tetrahydrofurane, 463 ml, 0.463 mol) was added drop wise to a cooled solution of methyl 6-methylnicotinate (20 g, 0.132 mol) and ethyl acetate (82 g, 0.927 mol) in dimethylformamide at −50° C.; gradually raised the temperature to r.t. and stirred at the same temperature. After 1 h, the reaction mixture was cooled to 0° C.; slowly diluted with 20% sulphuric acid and heated to reflux. After 4 h, the reaction mixture was cooled to r.t. and further to 0° C. and basified with potassium carbonate. The reaction medium was diluted with water and extracted in ethyl acetate (3×50 ml). Combined organic extract was dried over sodium sulphate and concentrated to afford crude 1-(6-methylpyridin-3-yl)ethan-1-one (compound I) (20.0 g) which was taken to next step without any purification.

ES-MS [M+1]+: 136.1

Sodium borohydride (2.3 g, 0.06 mol) was added in small portions over 30 min, to a solution of compound 1 (16.4 g, 0.121 mol) in ethanol (160 ml) at 0° C. and the reaction mixture was stirred at same temperature. After 1 h, the reaction mixture was diluted with sodium bicarbonate solution (sat) (2×200 ml) and extracted with dichloromethane (2×500 ml). The combined organic extract was dried over anhydrous sodium sulphate and concentrated to afford a pale yellow oil, which was purified by flash column chromatography (5% methanol/dichloromethane) to afford compound II (17.0 g; 93% yield over 2 steps) as a pale yellow oil.

ES-MS [M+1]+: 138.1

$^1$H NMR (400 MHz, CDCl$_3$): δ 8.35 (d, J=2.0 Hz, 1H), 7.63 (dd, J=8.0, 2.4 Hz, 1H), 7.12 (d, J=8.0 Hz, 1H), 4.89 (q, J=6.5 Hz, 1H), 3.30 (br s, 1H), 2.50 (s, 3H), 1.48 (d, J=6.5 Hz, 3H)

5-(1-methoxymethoxy-ethyl)-2-methyl-pyridine (III)

Compound II (15 g, 0.109 mol) was added, drop wise, to a cooled suspension of sodium hydride (6.56 g, 0.164 mol) in tetrahydrofurane (150 ml) and stirred at 0° C. After 30 min, chloromethyl methyl ether (13.2 g, 0.164 mol) was added drop wise while stirring and keeping the internal temperature around 0° C. After addition is over, the reaction mixture was stirred at the same temperature for 1 h. The reaction was quenched with ice cold water (80 ml) and extracted with ethyl acetate (3×50 ml). The combined organic extract was dried over anhydrous sodium sulphate and concentrated to afford an orange color oil, which was purified by flash column chromatography (1% methanol/dichloromethane) to afford compound III (10.0 g; 51% yield) as a pale yellow oil.

ES-MS [M+1]+: 182.2

$^1$H NMR (400 MHz, CDCl$_3$): δ 8.45 (d, J=2.0 Hz, 1H), 7.56 (dd, J=8.0, 2.0 Hz, 1H), 7.14 (d, J=8.0 Hz, 1H), 4.75 (q, J=6.4 Hz, 1H), 4.57 (ABq, 2H), 3.36 (s, 3H), 2.53 (s, 3H), 1.48 (d, J=6.6 Hz, 3H)

2-[5-(1-methoxymethoxy-ethyl)-pyridin-2-yl]-ethanol (IV)

A mixture of compound III (7.0 g, 0.0386 mol) and 37% formaldehyde solution (5.8 g, 0.077 mol) was heated to 160° C. in a sealed glass tube for 5 h. The reaction mixture was cooled to r.t. and concentrated under reduced pressure to afford a crude compound which was purified by flash column chromatography (1% methanol/dichloromethane) to afford compound IV (1.2 g; 17% yield) as pale yellow oil.

ES-MS [M+1]+: 212.1

$^1$H NMR (400 MHz, CDCl$_3$): δ 8.42 (d, J=2.0 Hz, 1H), 7.65 (dd, J=8.0, 2.4 Hz, 1H), 7.25 (d, J=8.0 Hz, 1H), 4.72 (q, J=6.6 Hz, 1H), 4.65 (t, J=5.6 Hz, 1H), 4.52 (ABq, 2H), 3.73 (m, 2H), 3.24 (s, 3H), 2.86 (t, J=7.2 Hz, 2H), 1.49 (d, J=6.4 Hz, 3H).

4-{2-[5-(1-methoxymethoxy-ethyl)-pyridin-2-yl]-ethoxy}-benzaldehyde (V)

Methanesulphonylchloride (1.19 g, 0.01 mol) was added, drop wise, to a cooled suspension of compound IV (1.7 g, 0.008 mol) and triethylamine (1.79 ml, 0.013 mol) in dichloromethane (20 ml) at 0° C. and stirred at same temperature for 1 h. The reaction mixture was diluted with water (50 ml) and extracted with dichloromethane (3×50 ml). The combined organic extract was dried over anhydrous sodium sulphate and concentrated to afford 2-(5-(1-(methoxymethoxy)ethyl)pyridin-2-yl)ethyl methanesulfonate (2.04 g; 88% yield) as a yellow oil, which was taken to next step without purification.

ES-MS [M+1]+: 290

2-(5-(1-(methoxymethoxy)ethyl)pyridin-2-yl)ethyl methanesulfonate was added (2.3 g, 0.008 mol) to a stirred suspension of 4-hydroxybenzaldehyde (1.65 g, 0.0137 mol) and potassium carbonate (1.86 g, 0.0137 mol) in mixture of toluene (25 ml) and ethanol (25 ml); stirred at 85° C. for 5 h. After consumption of the starting materials, the reaction mixture was diluted with water (30 ml) and extracted with ethyl acetate (2×100 ml). The combined organic extract was washed with water; dried over anhydrous sodium sulphate and concentrated to afford a crude dark yellow liquid. The crude was purified by flash column chromatography (1% methanol/dichloromethane) to afford compound V (1.5 g; 60% yield) as pale yellow liquid.

ES-MS [M+1]+: 316.1

5-(4-{2-[5-(1-methoxymethoxy-ethyl)-pyridin-2-yl]-ethoxy}-benzylidene)-thiazolidine-2,4-dione (VI)

Piperidine (80 mg, 0.95 mmol) was added to a solution of compound V (0.6 g, 1.9 mmol) and thiazolidine-2,4-dione (0.22 g, 1.9 mmol) in ethanol (15 ml) and the mixture was heated to reflux overnight. After 15 h, the reaction mixture was cooled to r.t. and concentrated under reduced pressure to afford crude mixture, which was purified by flash column chromatography (2% methanol/dichloromethane) to afford compound VI (500 mg; 64% yield) as a yellow solid.

ES-MS [M+1]+: 415.1

$^1$H NMR (400 MHz, DMSO-d$_6$): δ 12.25 (br s, 1H), 8.47 (d, J=2.0 Hz, 1H), 7.70 (dd, J=8.0, 2.0 Hz, 1H), 7.54 (d, J=8.8 Hz, 2H), 7.36 (d, J=8.0 Hz, 1H), 7.21 (d, J=8.8 Hz, 2H), 4.73 (m, 1H), 4.60-4.40 (m, 4H), 4.22 (t, J=6.2 Hz, 1H), 3.24 (s, 3H), 3.20 (t, J=6.8 Hz, 2H), 1.41 (d, J=6.0 Hz, 3H).

5-(4-{2-[5-(1-hydroxy-ethyl)-pyridin-2-yl]-ethoxy}-benzyl)-thiazolidine-2,4-dione (1)

A solution of sodium borohydride (115 mg, 3.017 mmol) in 0.2N sodium hydroxide (1.2 ml) was added slowly to a stirred solution of compound VI (0.5 g, 1.207 mmol), dimethylglyoxime (42 mg, 0.36 mmol) and CoCl$_2$.6H$_2$O (23 mg, 0.096 mmol) in a mixture of water (6 ml): tetrahydrofurane (6 ml) and 1M sodium hydroxide (1 ml) solution at 10° C. and after addition, the reaction mixture was stirred at r.t. After 1 h, the reaction color lightened and additional quantities of sodium borohydride (46 mg, 1.207 mmol) and CoCl$_2$.6H$_2$O (22 mg, 0.096 mmol) were added and stirring was continued at r.t. After 12 h, the reaction was neutralized with acetic acid (pH~7); diluted with water (10 ml) and extracted in ethyl acetate (3×50 ml). The combined organic extract was dried over anhydrous sodium sulphate and concentrated to afford crude compound VII, 5-(4-(2-(5-(1-(methoxymethoxy)ethyl)pyridin-2-yl)ethoxy)benzyl)thiazolidine-2,4-dione (0.4 g) as pale yellow semi solid, which was taken to next step without purification.

ES-MS [M+1]+: 417.5

2N HCl (2 ml) was added to a solution of compound VII (0.4 g, 0.96 mmol) in methanol (20 ml) and the mixture was heated to reflux. After 4 h, the reaction mixture was cooled to r.t.; concentrated under reduced pressure to afford a residue which was dissolved in water and the solution was neutralized using sodium bicarbonate solution (sat). The resulting white precipitate was collected by filtration to afford compound 1 (250 mg; 56% yield over 2 steps) as an off-white solid.

ES-MS [M+1]+: 373.4

$^1$H NMR (400 MHz, DMSO-$d_6$): δ 12.00 (br s, —NH), 8.46 (d, J=2.0 Hz, 1H), 7.66 (dd, J=8.0, 2.4 Hz, 1H), 7.30 (d, J=8.0 Hz, 1H), 7.13 (d, J=8.4 Hz, 2H), 6.86 (d, J=8.4 Hz, 2H), 5.25 (d, J=4.4 Hz, 1H), 4.86 (m, 1H), 4.75 (m, 1H), 4.30 (t, J=6.8 Hz, 2H), 3.30 (m, 1H), 3.14 (t, J=6.4 Hz, 2H), 3.04 (m, 1H), 1.34 (d, J=6.4 Hz, 3H).

Example 5: Mixture (c) of Compounds (2) and (4)) and (Mixture (c) of Compounds (3 and (4))

A mixture of compounds (2) and (4) (mixture (c)) and a mixture of compounds (3) and (5) (mixture (d)) were prepared according to Scheme 7.

The methyl chloromethyl ether group of (Z)-5-(4-(2-(5-(1-(methoxy-methoxy)ethyl)pyridin-2-yl)ethoxy)benzylidene)thiazolidine-2,4-dione (compound VI) was removed by treatment with aqueous HCl to give the racemic alcohol VIII.

The enantiomers contained in the racemic mixture of (Z)-5-(4-(2-(5-(1-hydroxyethyl)pyridin-2-yl)ethoxy)benzylidene)thiazolidine-2,4-dione (VIII) were separated by HPLC chiral chromatography to yield (R)-VIII and (S)-VIII.

(R)-VIII was then treated with a reducing mixture (CoCl$_2$-6H$_2$O, dimethylglyoxime, NaOH, sodium borohydride), (modified conjugate reduction protocol of Pfaltz), to yield mixture (c) comprising compounds (2) and (4).

(S)-VIII was then treated with a reducing mixture (CoCl$_2$-6H$_2$O, dimethylglyoxime, NaOH, sodium borohydride), (modified conjugate reduction protocol of Pfaltz), to yield mixture (d) comprising compounds (3) and (5).

Scheme 7

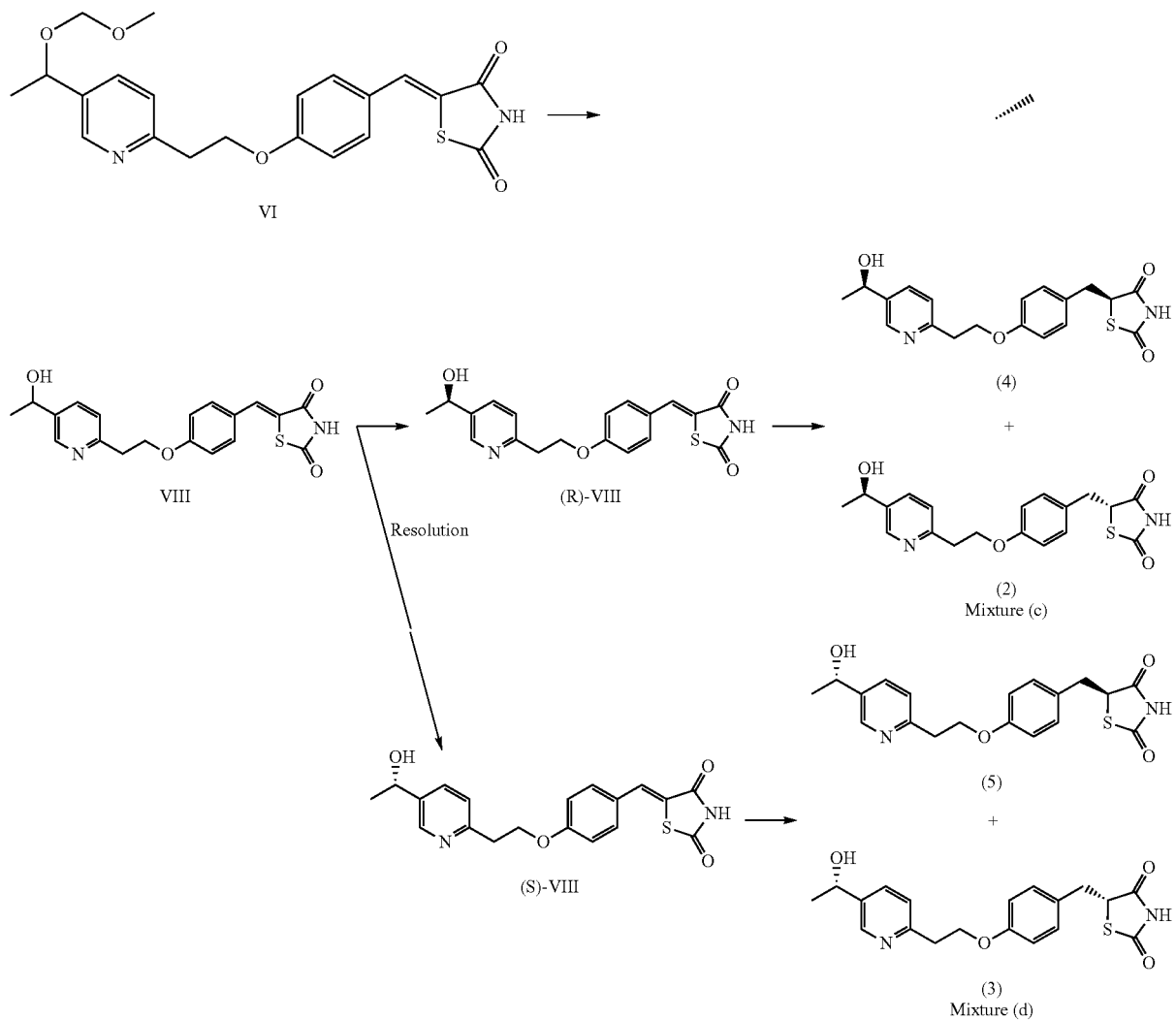

Example 6: Preparation of Diastereomeric Mixtures D-1 and D-2 of M-IV

Scheme 1:

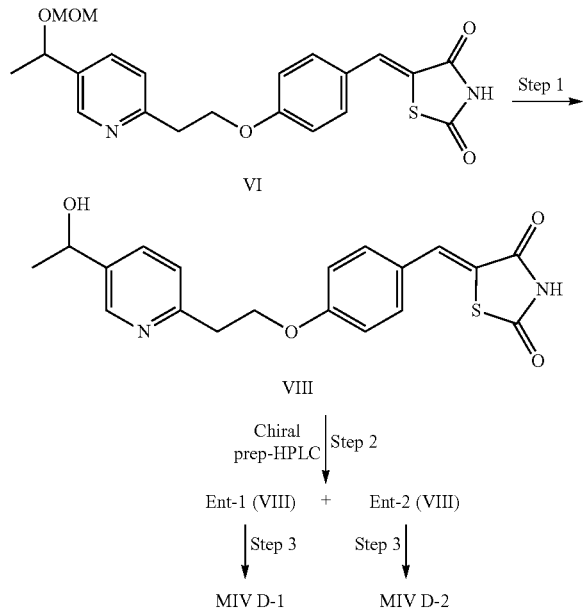

Step 1: Synthesis of Compound VIII:

HCl (48 ml, 2N) was added to a solution of compound VI (10 g, 0.024 mol) in methanol (200 ml) and the mixture was heated to reflux. After 4 h of reflux, the reaction mixture was cooled to r.t. and concentrated under reduced pressure to afford a yellow solid. The solid was suspended in water (70 ml) and neutralized using a saturated $NaHCO_3$ solution. The resulting pale yellow precipitate was collected by filtration and vacuum dried to afford compound VIII (7.5 g; 84% yield).

ES-MS [M+1]: 371.0.

Step 2: Chiral Prep. HPLC

Compound VIII (1.0 g) was dissolved in a mixture containing equal volumes of acetonitrile, methanol and dichloromethane; injected (150 µl injections) in chiral prep-HPLC column (Chiralpak-IA 250×20 mm, 5 micron) and separated [Mobile phase—n-Hexane/0.05% $Et_3N$ in EtOH (50:50); flow Rate: 18 ml/min; run time: 60 min]. The fractions containing the enantiomers VIIIa and VIIIb were separately concentrated under reduced pressure to minimum volume and the respective residues were diluted with EtOAc (100 ml), followed by water (50 ml). The resultant organic phases were dried over anhydrous $Na_2SO_4$ and concentrated to afford compounds VIIIa and VIIIb as off-white solids. Enantiomers VIIIa and VIIIb were isolated but the absolute configuration of each enantiomer has not been determined.

Compound Ent-1 (VIII): 250 mg (Yield: 50%); $t_R$ (Chiral HPLC)=14.8 min; ES-MS [M+1]+: 371.0; $^1H$ NMR (400 MHz, DMSO-$d_6$): δ 12.5 (br S, 1H), 8.47 (s, 1H), 7.71 (s, 1H), 7.67 (dd, J=8.0, 2.0 Hz, 1H), 7.53 (d, J=9.2 Hz, 2H), 7.31 (d, J=7.6 Hz, 1H), 7.08 (d, J=8.8 Hz, 2H), 5.25 (d, J=4.0 Hz, 1H), 4.74-4.76 (m, 1H), 4.43 (dd, J=6.8, 6.4 Hz, 2H), 3.18 (t, J=6.4 Hz, 2H), 1.34 (d, J=6.4 Hz, 3H).

Compound Ent-2 (VIII): 237 mg (Yield: 47%); $t_R$ (Chiral HPLC)=16.7 min; ES-MS [M+1]+: 371.0; $^1H$ NMR (400 MHz, DMSO-$d_6$): δ 12.5 (br S, 1H), 8.47 (s, 1H), 7.71 (s, 1H), 7.67 (dd, J=8.0, 2.0 Hz, 1H), 7.53 (d, J=8.8 Hz, 2H), 7.31 (d, J=8.0 Hz, 1H), 7.08 (d, J=9.2 Hz, 2H), 5.23 (d, J=3.6 Hz, 1H), 4.75 (m, 1H), 4.43 (dd, J=6.8, 6.4 Hz, 2H), 3.18 (dd, J=6.8, 6.4 Hz, 2H), 1.34 (d, J=6.4 Hz, 3H).

Synthesis of Diastereomeric Mixtures of M-IV

Synthesis of D-1 MIV

Step 3:

A solution of $NaBH_4$ (77 mg, 2.02 mmol) in 0.1 N NaOH (2 ml) was added slowly to a stirred solution of compound Ent-1 (VIII) (250 mg, 0.675 mmol), dimethylglyoxime (32 mg, 0.27 mmol) and $CoCl_2.6H_2O$ (16 mg, 0.067 mmol) in a mixture of water (10 ml), THF (10 ml) and 1M NaOH (0.5 ml) solution at 10° C., and the reaction mixture was stirred at r.t. for 1 h. After color of the reaction medium faded, additional quantity of $NaBH_4$ (26 mg, 0.675 mmol) and $CoCl_2.6H_2O$ (16 mg, 0.067 mmol) were added and stirring was continued at r.t. [additional quantities of $CoCl_2$ and $NaBH_4$ were added at 12 h intervals till the starting material was consumed, as monitored by LCMS]. After 90-96 h, the reaction mixture was neutralized with AcOH (pH~7); diluted with water (10 ml) and extracted in EtOAc (3×50 ml). The combined organic extract was dried over anhydrous $Na_2SO_4$ and concentrated to afford crude compound which was purified by flash column chromatography ($SiO_2$; 4% methanol in $CH_2Cl_2$) to afford diastereomeric mixture of MIV D-1 (125 mg) as off-white solid.

Synthesis of D-2 MIV

Step 3:

A solution of $NaBH_4$ (72 mg, 1.921 mmol) in 0.1 N NaOH (2 ml) was added slowly to a stirred solution of compound Ent-2 (VIII) (237 mg, 0.64 mmol), dimethylglyoxime (30 mg, 0.256 mmol) and $CoCl_2.6H_2O$ (15 mg, 0.064 mmol) in a mixture of water (10 ml), THF (10 ml), and 1M NaOH (0.5 ml) solution at 10° C., and the reaction mixture was stirred at r.t. for 1 h. After color of the reaction medium faded, additional quantity of $NaBH_4$ (24 mg, 0.64 mmol) and $CoCl_2.6H_2O$ (15 mg, 0.064 mmol) were added and stirring was continued at r.t. [additional quantities of $CoCl_2.6H_2O$ and $NaBH_4$ were added at 12 h intervals till the starting material was consumed, as monitored by LCMS]. After 96 h, the reaction mixture was neutralized with AcOH (pH~7); diluted with water (10 ml) and extracted in EtOAc (3×50 ml). The combined organic extract was dried over anhydrous $Na_2SO_4$ and concentrated to afford crude compound, which was purified by flash column chromatography ($SiO_2$; 4% methanol in $CH_2Cl_2$) to afford diastereomeric mixture of MIV D-2 (100 mg) as off-white solid.

MIV D-1: yield: 125 mg (50%); $t_R$ (Chiral HPLC)=17.8, 14.7 min; ES-MS [M+1]+: 373.0, $^1H$ NMR (400 MHz, DMSO-$d_6$): δ 12.00 (br s, NH), 8.46 (d, J=2.0 Hz, 1H), 7.67 (dd, J=8.0, 2.4 Hz, 1H), 7.30 (d, J=8.0 Hz, 1H), 7.13 (d, J=8.8 Hz, 2H), 6.86 (d, J=8.4 Hz, 2H), 5.27 (d, J=4.0 Hz, 1H), 4.88-4.85 (m, 1H), 4.76-4.74 (m, 1H), 4.30 (t, J=6.8 Hz, 2H), 3.30 (m, 1H), 3.14 (dd, J=6.8, 6.4 Hz, 2H), 3.08-3.02 (m, 1H), 1.34 (d, J=6.4 Hz, 3H).

MIV D-2: yield: 100 mg (42%); $t_R$ (Chiral HPLC)=19.4, 16.5 min; ES-MS [M+1]+: 373.0; $^1H$ NMR (400 MHz, DMSO-$d_6$): δ 12.01 (br s, —NH), (d, J=2.0 Hz, 1H), 7.67 (dd, J=8.0, 2.0 Hz, 1H), 7.31 (d, J=8.0 Hz, 1H), 7.13 (d, J=8.8 Hz, 2H), 6.86 (d, J=8.8 Hz, 2H), 5.27 (d, J=4.0 Hz, 1H), 4.88-4.85 (m, 1H), 4.76-4.74 (m, 1H), 4.30 (dd, J=6.8, 6.4 Hz, 2H), 3.30 (m, 1H), 3.14 (dd, J=6.8, 6.4 Hz, 2H), 3.08-3.02 (m, 1H), 1.34 (d, J=6.8 Hz, 3H).

Diastereomeric mixtures D-1 and D-2 of MIV correspond to mixtures (c) and (d) described above, but the specific diastereomers present in each diastereomeric mixture have not been assigned.

Example 7: In Vitro ADME and Toxicological Characterization

Protocol: The assays performed include cytochrome P450 inhibition with the different isoforms, microsomal and hepatocyte stability, neurotoxicity in neural cells and hERG safety assays using a patch clamp electrophysiology measurement (FDA Draft Guidance for Industry. Drug Interaction Studies—Study Design, Data Analysis, Implications for Dosing, and Labelling Recommendations 2012, The European Medicines Agency (EMA) Guideline on the Investigation of Drug Interactions Adopted in 2012, Schroeder K et al. 2003 J Biomol Screen 8 (1); 50-64, Barter Z E et al. 2007 Curr Drug Metab 8 (1); 33-45, LeCluyse E L and Alexandre E 2010 *Methods Mol Biol* 640; 57-82). The results indicate a safe and favourable ADME profile for the compounds of the invention.

Example 8

The brain plasma ratios of Pioglitazone, MIV, MIII and MII following oral dosing of a single administration of Pioglitazone at 4.5 mg/kg in male C57BL/6 mice.

The brain-plasma ratio was calculated based on levels of Pioglitazone, MIV, MIII and MII in plasma and brain quantified at C max (maximal concentration) following oral dosing of a single administration of Pioglitazone at 4.5 mg/kg in male C57BL/6 mice.

Figure 4:
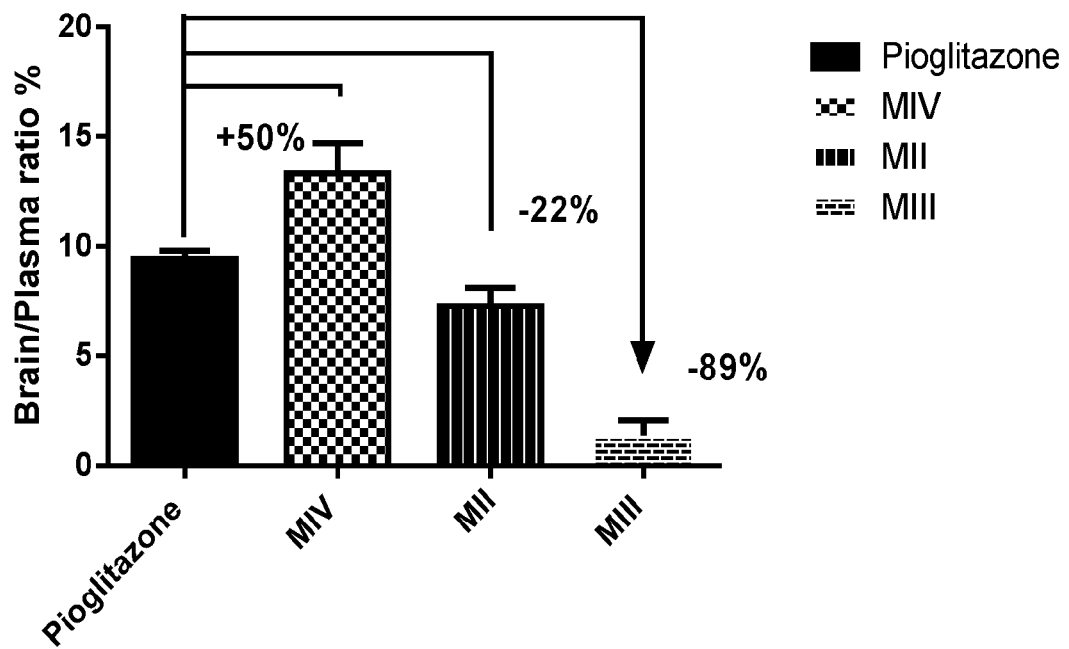
FIG. 4 represents the brain plasma ration calculated based on levels of Pioglitazone, MIV, MIII and MII in plasma and brain quantified at Cmax (maximal concentration) following oral dosing of a single administration of Pioglitazone at 4.5 mg/kg in male C57BL/6 mice.

The percentage brain plasma ratio was 9, 13, 7 and 1%, respectively, for Pioglitazone, MII and MIII as shown in the FIG. 4. Thus, active metabolites MIII and MII crossed the BBB at much lower extent than Pioglitazone as it was predicted based on the physicochemical properties of the compounds (see Table1). In contrast, unexpectedly metabolite MIV crossed the BBB in a higher percentage than the parent compound Piolgitazone The calculations of the both indexes (C log P and QP log BB) for Pioglitazone and its metabolites MII and MIII are shown in Table 1. For both indexes the 2 metabolites are lower than for pioglitazone, suggesting for MII, and MIII a less favored penetration and distribution within CNS.

TABLE 1

| Structure | Name | QPlogBB | CLogP | HBD | HBA |
|---|---|---|---|---|---|
| 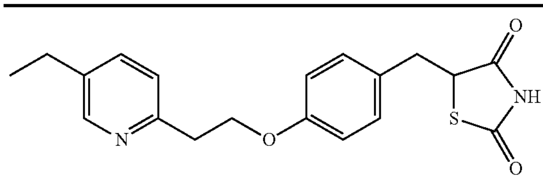 | Pioglitazone | −1.22 | 3.53 | 1 | 4 |
| 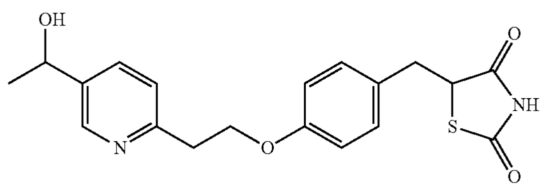 [SMILES: CC(O)c1ccc(CCOc2ccc(CC3SC(=O)NC3=O)cc2)nc1] | MIV | −1.72 | 1.78 | 2 | 5 |
| 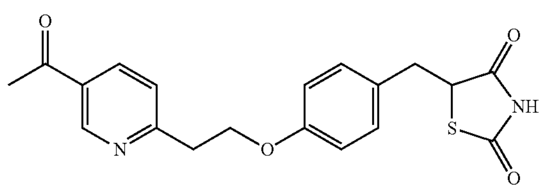 [SMILES: CC(=O)c1ccc(CCOc2ccc(CC3SC(=O)NC3=O)cc2)nc1] | MIII | −1.66 | 2.34 | 1 | 5 |
| 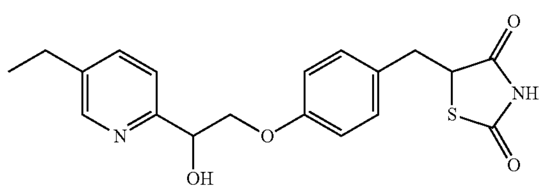 [SMILES: CCc1ccc(C(O)COc2ccc(CC3SC(=O)NC3=O)cc2)nc1] | MII | −1.72 | 2.13 | 2 | 5 |

Example 9

The brain plasma ratios of Pioglitazone and MIV and following oral dosing of a single administration of either Pioglitazone or M-IV both at 4.5 mg/kg in male C57BL/6 mice.

In order to confirm the findings showed in the last example, additional experiments were done. The brain-plasma ratio was calculated based on the pharmacokinetics curves of plasma and brain concentration-time profiles calculated as area under the curves of Pioglitazone and following oral dosing of a single administration of either Pioglitazone or MIV both at 4.5 mg/kg in male C57BL/6 mice.

Figure 5:
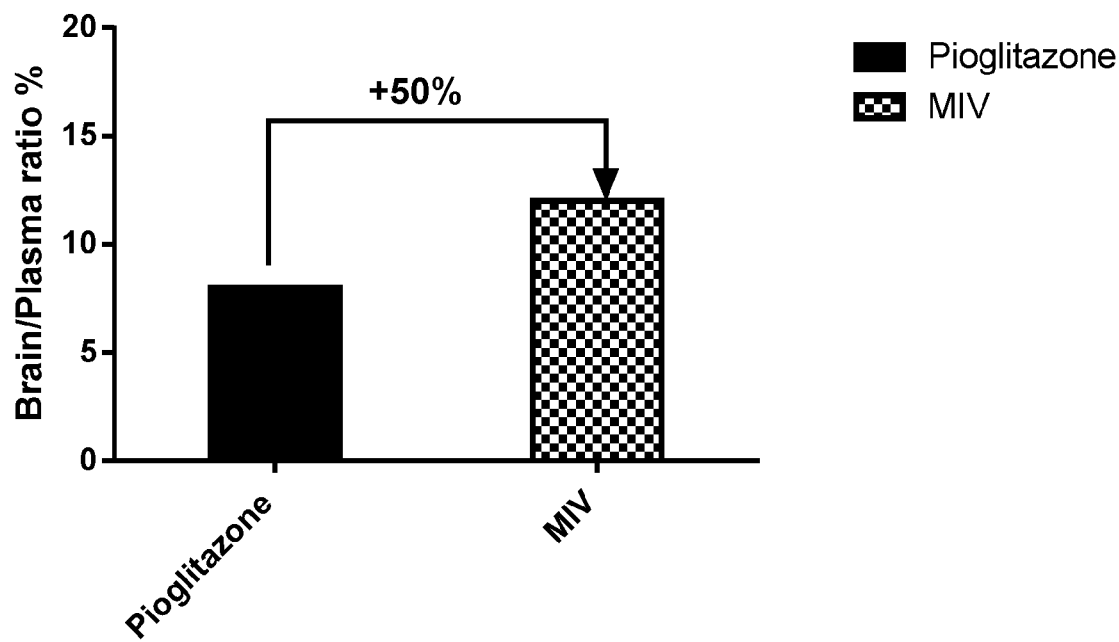
FIG. 5 represents the brain plasma ration calculated based on the pharmacokinetics curves of plasma and brain concentration-time profiles calculated as area under the curves of Pioglitazone and following oral dosing of a single administration of either Pioglitazone or MIV both at 4.5 mg/kg in male C57BL/6 mice.

The percentage brain-plasma ratio was 8% and 12% for Pioglitazone and M4 respectively as shown in the FIG. 5. This 50% of increase in brain-plasma ratio for the hydroxilated metabolite M-IV compared with that the one observed with Pioglitazone under the same condition, was totally unexpected based on the on the physicochemical properties predictive calculations (see Table 1).

M-IV shows a behavior contrary to that expected. As MII, MIV is a monohydroxylated metabolite, but instead of decreasing around 50% its BBB penetration, the BBB penetration is 50% higher.

The calculations of the both indexes (C log P and QP log BB) for Pioglitazone and M-IV are shown in Table 1. For both indexes MIV shows a lower value than pioglitazone, suggesting for M-IV a less favored penetration and distribution within CNS, contrary to what has surprisingly been observed experimentally.

Example 10: Characterization of In Vivo Epimerization of the Two Diastereomeric Mixtures of MIV, D-1 and D-2 in Mice Protocol: Pharmacokinetic parameters of diastereomeric mixtures D-1 and D-2 of 5-(4-(2-(5-(1-hydroxyethyl)pyridine-2-yl)ethoxy)benzyl)thiazolidine-2,4-dione following single oral (4.5 mg/kg) gavage dose administration to male Swiss albino mice were determined. A total of 51 mice were used in this study with parallel sampling design (n=3/time point). Blood samples and were collected pre-dosing and different times post dosing for both oral pharmacokinetics.

Diastereomeric mixtures D-1 and D-2 of 5-(4-(2-(5-(1-hydroxyethyl)pyridine-2-yl)ethoxy)benzyl)thiazolidine-2,4-dione were extracted from Swiss albino mouse plasma samples using liquid-liquid extraction (LLE) method and quantified using liquid chromatography tandem mass spectrometry (LC-MS/MS) with Electro Spray Ionization (ESI) and multiple reaction monitoring (MRM). Selected plasma and brain samples were subjected for the chiral analysis using Chiral AGP column to identify the chiral inter-conversion. Achiral bioanalytical method was employed to quantify the total M-IV present in the plasma and brain samples.

Formulation samples were suitably diluted with 70% methanol and the instrument response was compared against known corresponding diastereomeric mixture standard using achiral LC-MS/MS method. The lower limit of quantification (LLOQ) in plasma for diastereomeric mixture D-1 and D-2 of 5-(4-(2-(5-(1-hydroxyethyl)pyridine-2-yl)ethoxy)benzyl)thiazolidine-2,4-dione (1) is 0.99 ng/mL. Pharmacokinetic parameters were calculated using the non-compartmental analysis tool of Phoenix WinNonlin.

Figure 6:
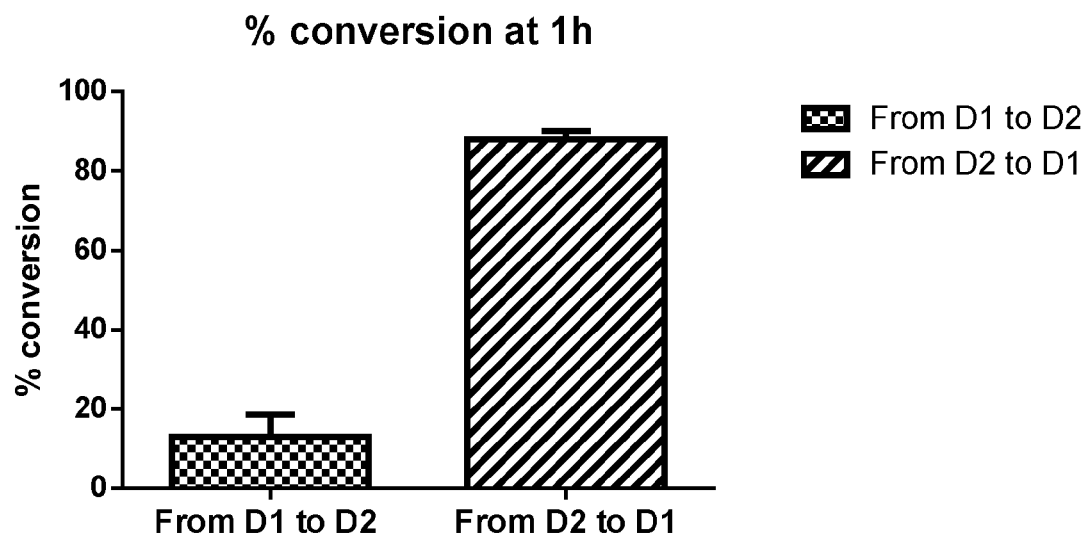
FIG. 6 represents the concentrations of mixture (c) comprising compounds (2) and (4) and mixture (d) comprising compounds (3) and (5) in plasma of a C57BL/6 mouse after a single oral administration of 4.5 mg/Kg of said mixtures.

The results from these experiments are shown in FIG. 6. The data clearly demonstrates that the difference in % of conversion among diastereomeric mixtures is high in mice. In vivo, both D-1 and D-2 interconvert, although the conversion to D-2 from D-1 is much more accentuated than the conversion from D-1 to D-2.

Example 11: Characterization of Cortical Neurons Glutamate Injured as a Model of Alzheimer's Disease Primary cortical neurons injured by glutamate (excitotoxicity) are a well established in vitro model for neurodegenerative disorders (*J Neurosci;* 1999 Apr. 1; 19(7):2455-63; *J Neurosci Res.* 2013 May; 91(5):706-16) such as Parkinson's disease, Alzheimer's disease, and Huntington's disease (*Brain Res Bull* 2013 April; 93:27-31.), but also in other pathologies such as multiple sclerosis (*Scand J Immunol* 2014; 79(3):181-186).

Protocol: Rat cortical neurons were cultured as described by Singer (J Neurosci. 1999 Apr. 1; 19(7):2455-63) and Callizot (J Neurosci Res. 2013 May; 91(5):706-16).

Foetuses were collected and immediately placed in ice-cold Leibovitz medium. Cortex was treated with a trypsin-EDTA solution and the dissociation was stopped by addition of Dulbecco's modified Eagle's medium (DMEM) with glucose (Pan Biotech), containing DNAse I and 10% fetal calf serum (FCS). Cells were mechanically dissociated and centrifuged. The pellet was resuspended in a defined culture medium with 10 ng/ml of brain-derived neurotrophic factor (BDNF). The cells were seeded in 96-well plates precoated with poly-L-lysine and were cultured at 37°. The medium was changed every 2 days. The cortical neurons were intoxicated with glutamate after 13 days of culture.

Briefly, on day 13 of culture, BDNF and test compound were pre-incubated with primary cortical neurons for 1 hour before glutamate exposure. Glutamate was added to a final concentration of 40 µM diluted in control medium in presence of BDNF or test compound for 20 min.

After 20 min, glutamate was washed out and fresh culture medium with BDNF or test compound was added for additional 48 hours. The survival evaluation was done by a MTT assay performed with CellTiter 96® Aqueous One Solution Cell Proliferation Assay (Promega).

Figure 7:
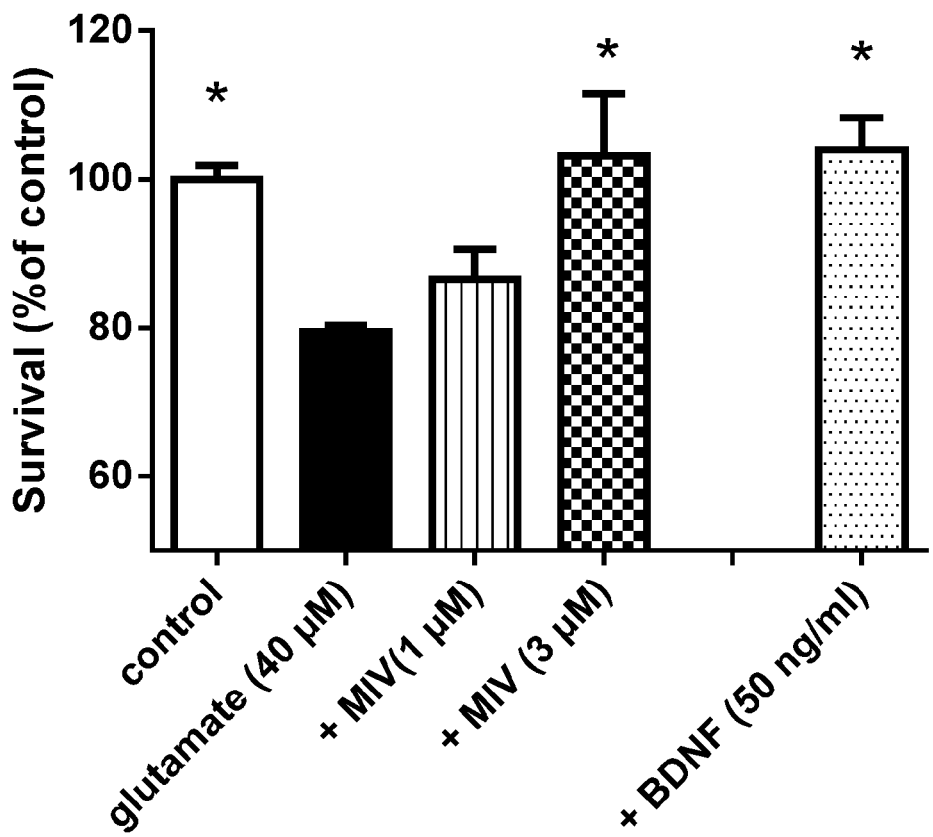
FIG. 7 represents the effect of compound of formula (1) in primary rat cortical neurons injured by glutamate.
Figure 8:
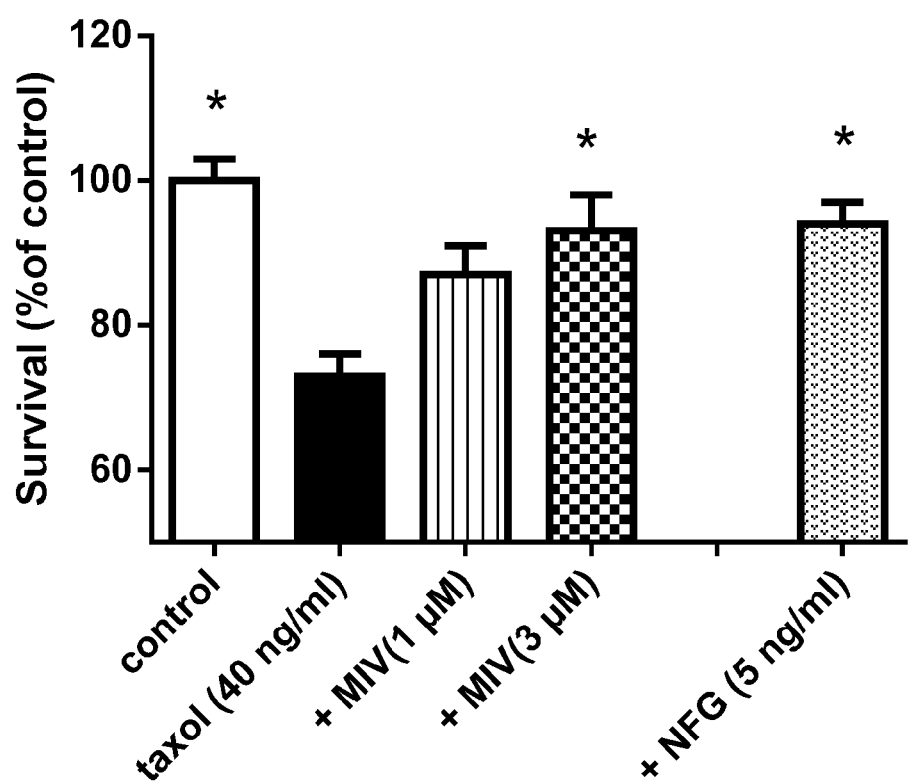
FIG. 8 represents the effect of compound of formula (1) in primary culture of sensory neurons injured by Paclitaxel (Taxol).

The results are shown in FIG. 7. They show that on a glutamate injury, MIV (compound (1)) shows a protective effect (reaching the significance for the 3 µM). Interestingly we observed a nice bell shape curve for MIV. At 3 µM we have a full protective effect as the one observed with the reference compound (BDNF 50 ng/ml). All values are expressed as mean+/−SE. Statistical analysis was performed by one-way ANOVA, followed by Dunnett's or PLSD Fisher test, $p<0.05$ are considered significant.

Example 12: Characterization of Inhibition of MAO B (Monoamine Oxidases) as a Potential Drug for Treating Parkinson's Disease Selective inhibitors MAO-B increase dopamine levels in the CNS affected in Parkinson's disease without increasing levels of the other neurotransmisors (epinephrine, norepinephrine or serotonine), in contrast to no selective MAO inhibitors (MAO-A and MAO B). The MAO-B inhibitors can be used also to treat depressions.

Protocol: Human recombinant monoamine oxidase proteins MAO-A and MAO-B were purchased from Sigma Aldrich (Reference M7316 and M7441 respectively). In order to monitor the MAO enzymatic activities and their inhibition rate a fluorescence based assay was used. The substrate for the assay, kynuramine, is non-fluorescent until undergoing oxidative deamination by MAOs resulting in the fluorescent product 4-hydroxyquinoline. Kynuramine is a substrate for both MAO-A and -B (non-specific substrate). Clorgiline and Deprenyl (Sigma Aldrich) were used as controls for specific inhibition of MAO-A and MAO-B respectively.

Results show that 5-(4-(2-(5-(1-hydroxyethyl)pyridine-2-yl)ethoxy)benzyl)thiazolidine-2,4-dione inhibits MAO B with a $IC_{50}$ of 70.5 nM. In contrast, this compound did not inhibit MAO A protein.

Example 13: Characterization of In Vivo Efficacy in an Animal Model Experimental Autoimmune Encephalomyelitis (EAE) as a Model of Neuroinflammatory Diseases Neuroinflammation can be initiated in response to a variety of infection, traumatic brain injury, toxics, or autoimmunity in the CNS.

The neuroinflammatory models are characterized by proliferation of astrocytes and microglia, along with neuronal loss, is a prominent feature of many diseases of the central nervous system, including Alzheimer's Disease, Multiple Sclerosis, stroke, Parkinson, traumatic brain injury, infection and ALD (Human Molecular Genetics, 2004, Vol. 13, No. 23 2997-3006).

Chronic inflammation is the sustained activation of glial cells and recruitment of other immune cells into the brain. It is chronic inflammation that is typically associated with neurodegenerative diseases.

The EAE model is a neuroinflammatory model, classically used for multiple sclerosis, which resembles and includes most of the features of the severe cerebral forms of ALD, microglial activation, brain demyelination and axonal degeneration as well. Although the ethiology of the disease is different from ALD and the EAE (a model of multiple sclerosis triggered by autoreactive CD4+ lymphocytes), the EAE model is a valuable tool for studying therapies for both ALD and multiple sclerosis (Nature 2007; 7:904-912).

Protocol: The development of clinical symptoms in multiple sclerosis and its animal model experimental autoimmune encephalomyelitis (EAE) involves T-cell activation and migration into the central nervous system, production of glial-derived inflammatory molecules, and demyelination and axonal damage. Chronic, monophasic EAE was actively induced as described with greater than 98% pure synthetic myelin oligodendrocyte glycoprotein peptide 35-55 (MOG35-55, MEVGWYRSPFSRWHLYRNGK, SEQ ID NO: 1). Female C57BL/6 mice (6-8 weeks old) were injected (two 100 µL subcutaneous injections into one hind limb) with 250 µg of MOG35-55 emulsified in a 100 µL phosphate-buffered solution mixed with 100 µL of complete Freund's adjuvant containing 500 µg of *Mycobacterium tuberculosis* (Difco, Detroit, Mich.). The mice received an injection of pertussis toxin (400 ng in 200 µL of a phosphate-buffered solution, intraperitoneally), a second pertussis toxin injection 2 days later, and a booster injection of MOG35-55 at 7 days. Clinical signs were scored as follows: 0, no signs; 1.0, limp tail/loss of righting; 2.0, ataxia with limp tail; 3.0, paralysis of single hind limb; 4.0, paralysis of both hind limbs; 4.5, moribund; and 5.0, death. For both models, scores of 5 were noted and counted on the day of death only.

The compound was administered twice a day (bid) started on day 5 post immunization for 15 days at three different increasing doses.

Figure 9:
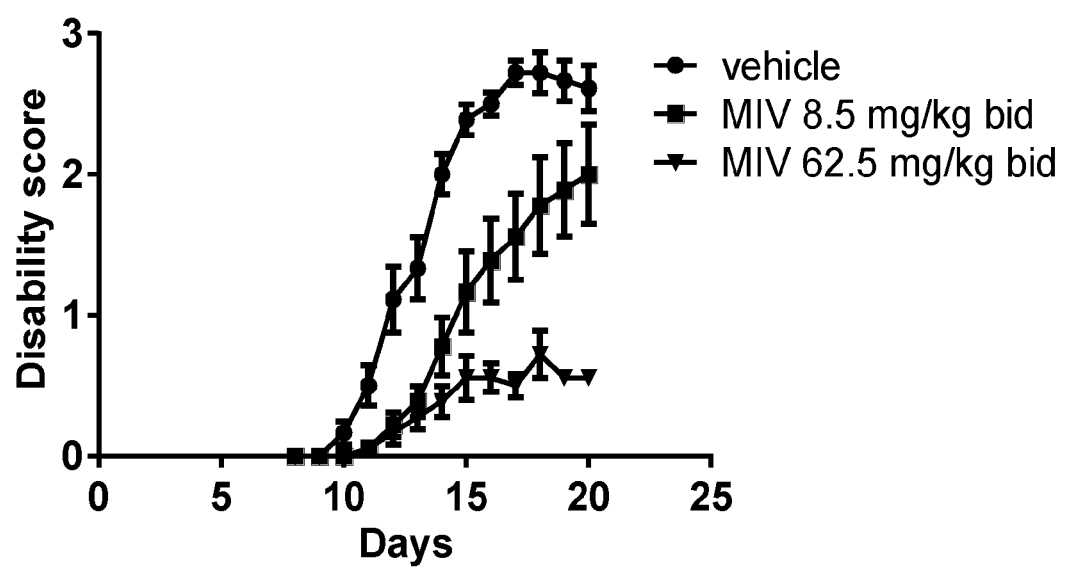
FIG. 9 represents the effect of compound of formula (1) in the disability score in an in vivo efficacy study in an experimental autoimmune encephalomyelitis (EAE) of multiple mouse model.

The results showed that MIV (compound (1)) reduces the development and severity of experimental autoimmune encephalomyelitis model. Average daily clinical scores from the experiment are shown in FIG. 9. The clinical symptoms decreases in a dose-dependent manner, the highest doses show the maximal effect. Clinical symptoms were reduced by MIV, suggesting a role for PPARgamma activation in protective effects. No body weight loss and no significant hematological toxicity at highest doses associated to treatment.

Neuroinflammation is a hallmark of both multiple sclerosis and ALD, thus MIV may be effective on both diseases. In fact, decreasing microglia activation provides a molecular basis for explaining why allogeneic and autologous HSCT are effective at arresting the cerebral inflammation, namely by the replacement and the functional metabolic restoration of the monocyte lineage and connect cALD and AMN phenotypes with a shared pathogenic pathway (Human Molecular Genetics, 2012, Vol. 21, No. 5 1062-1077). Thus, these models may be have a great potential and relevance to study the role of PPAR gamma agonists in ALD.

Example 14: Characterization in Fibroblasts from Patients of X-ALD as a Model of X-Linked Adrenoleukodystrophy Human control and X-linked adrenoleukodystrophy fibroblasts were obtained from Coriell (Candem, USA). Cells were grown in Dulbecco's modified Eagle medium containing 10% foetal bovine serum, 100 U/ml penicillin and 100 mg streptomycin, at 37° C. in humidified 95% air/5% $CO_2$, to 80-90% confluence. To perform our experiments, Dulbecco's modified Eagle medium without D-glucose, pyruvate or L-glutamine was used. Cells were cultured in this medium supplemented with 1 g/l of glucose or 1 g/l of galactose and 10% foetal bovine serum for 24 hours incubated with increasing doses of MIV (3, 10 and 30 µM).

The determination of MTT was performed as described by Mosmann *J. Immunol. Methods* 1983, 65, 55-63 and by Hansen *J. Immunol. Methods* 1989; 119, 203-210. This method is based on the ability of viable but not dead cells to convert the tetrazolium salt (MTT) to colored formazan.

For the determination of ATP levels, $2\times10^4$ cells/well were seeded in 96 well cell culture plate in complete medium. After 16-18 h cells, were lysed in 20 µl lysis buffer and 10 µl of lysate was used to measure ATP levels using ATP determination Kit (Molecular Probes, Invitrogen). 1 µl each of the remaining lysate was used for protein measurement.

Results show a protective effect of MIV (compound (1)) on ALD fibroblasts based on increase in cell survival (20% at 3, M, vs non-treated).

Example 15: Characterization of Spinal Cord Motor Neurons as a Model of Motor Neuron Diseases (ALS)

Spinal cord motor neurons injured by glutamate are an in vitro experimental model suitable for studying ALS and other motor neuron diseases (MNDs) such as Progressive bulbar palsy, pseudobulbar palsy, primary lateral sclerosis (PLS), progressive muscular atrophy, spinal muscular atrophy (SMA), post-polio syndrome (PPS) and other rare diseases such us Charcot-Marie-Tooth disease, Guillain-Barré syndrome or AMN (*Neuron.* 1992 April; 8(4):737-44).

Protocol: Rat spinal cord (SC) motor neurons were cultured as described by Martinou (Neuron. 1992 April; 8(4): 737-44) and Wang (PLoS Genet. 2013; 9(9)). Briefly, pregnant female rats of 14 days gestation were killed by cervical dislocation and foetuses were collected and immediately placed in ice-cold L15 Leibovitz medium. Spinal cord was treated for 20 min at 37° C. with a trypsin-EDTA. The dissociation was stopped by addition of Dulbecco's modified Eagle's medium (DMEM) with glucose (Pan Biotech), containing DNAse I and 10% fetal calf serum (FCS). Cells were mechanically dissociated and they were then centrifuged. The pellet was resuspended in a defined culture medium with 10 ng/ml of brain-derived neurotrophic factor (BDNF). The cells were seeded in 96-well plates precoated with poly-L-lysine and were cultured at 37°. The medium was changed every 2 days.

Briefly, on day 13 of culture, BDNF or test compound was pre-incubated with primary Spinal cord (SC) motor neurons for 1 hour before glutamate exposure. Glutamate was added to a final concentration of 10 µM diluted in control medium in presence of BDNF or test compound for 20 min. After 20 min, glutamate was washed out and fresh culture medium with BDNF or test compound was added for additional 48 hours.

The survival evaluation was done by immunostaining. 48 after the intoxication, the cell culture supernatant was taken off and the SC motor neurons were fixed by a cold solution of ethanol (95%) and acetic acid (5%) for 5 min and permeabilized. Cells were incubated for 2 hours with a monoclonal antibody anti microtubule-associated-protein 2 (MAP-2) that stains specifically cell bodies of neurons (MAP-2) allowing study of neuron survival evaluation in the culture. This antibody was revealed with Alexa Fluor 488 goat anti-mouse IgG).

For each condition 6 wells were assessed, 30 pictures per well were taken using ImageXpress (Molecular Device) with 20× magnification. All images were taken with the same conditions. Analysis of total number of neurons was performed automatically by using Custom module editor (Molecular Device).

Test compounds were pre-incubated for 1 hour before glutamate application.

Figure 10:
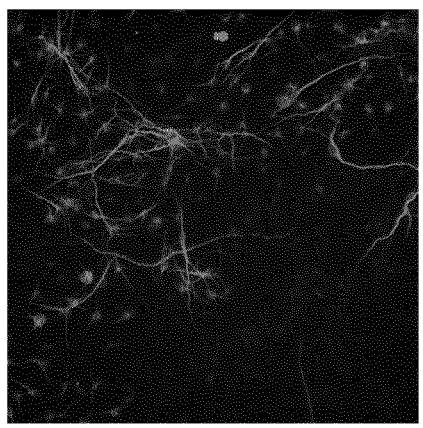
FIG. 10 represents the effect of compound of formula (1) in primary motor neurons injured by glutamate
Figure 10:
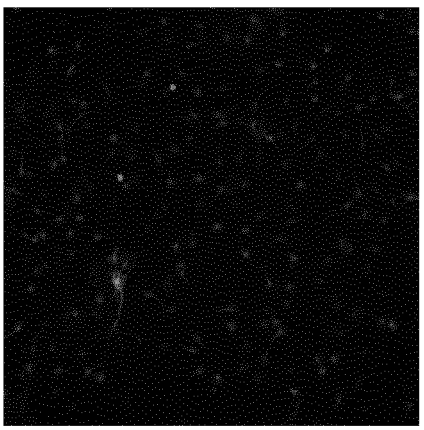
Figure 10:
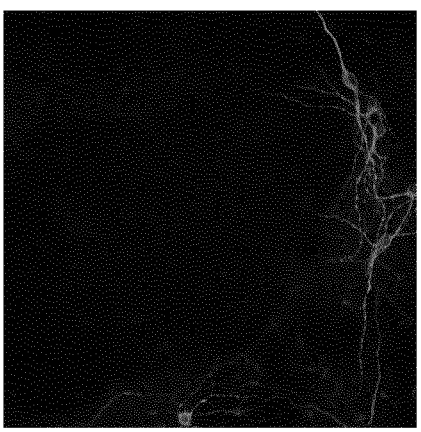

The results (FIG. 10) showed that MIV (compound (1), 1 µM) on a glutamate injury has a protective effect in SC motor neurons (MN), demonstrated by a statistically different (p<0.05 t Student's) increase in cell survival vs the control with glutamate (Glut).

---

---

The invention claimed is:

1. A method of treatment of a central nervous system disorder, comprising administering to a subject in need thereof a dosage form comprising an effective amount of a compound of formula (1)

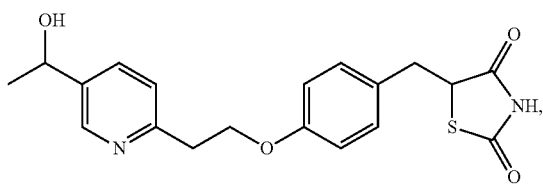

(1)

or a pharmaceutically acceptable salt thereof, wherein the central nervous system disorder is adrenoleukodystrophy (ALD or X-ALD), amyotrophic lateral sclerosis (ALS), Parkinson's disease, or multiple sclerosis.

2. The method according to claim 1, wherein the compound of formula (1) is
    (2) (R)-5-(4-(2-(5-((R)-1-hydroxyethyl)pyridine-2-yl)ethoxy)benzyl)thiazolidine-2,4-dione;
    (3) (R)-5-(4-(2-(5-((S)-1-hydroxyethyl)pyridine-2-yl)ethoxy)benzyl)thiazolidine-2,4-dione;
    (4) (S)-5-(4-(2-(5-((R)-1-hydroxyethyl)pyridine-2-yl)ethoxy)benzyl)thiazolidine-2,4-dione; or
    (5) (S)-5-(4-(2-(5-((S)-1-hydroxyethyl)pyridine-2-yl)ethoxy)benzyl)thiazolidine-2,4-dione,
    or a pharmaceutically acceptable salt thereof.

3. A method of treatment of a central nervous system disorder, comprising administering to a subject in need thereof a dosage form comprising an effective amount of a mixture of two or more compounds selected from the group consisting of:
    compound (2): (R)-5-(4-(2-(5-((R)-1-hydroxyethyl)pyridine-2-yl)ethoxy)benzyl)thiazolidine-2,4-dione;
    compound (3): (R)-5-(4-(2-(5-((S)-1-hydroxyethyl)pyridine-2-yl)ethoxy)benzyl)thiazolidine-2,4-dione;
    compound (4): (S)-5-(4-(2-(5-((R)-1-hydroxyethyl)pyridine-2-yl)ethoxy)benzyl)thiazolidine-2,4-dione; and
    compound (5): (S)-5-(4-(2-(5-((S)-1-hydroxyethyl)pyridine-2-yl)ethoxy)benzyl)thiazolidine-2,4-dione,
    or a pharmaceutically acceptable salt thereof, wherein the mixture is optically active, wherein the central nervous system disorder is adrenoleukodystrophy (ALD or X-ALD), amyotrophic lateral sclerosis (ALS), Parkinson's disease, or multiple sclerosis.

4. The method according to claim 3, wherein the mixture comprises
    (a) said compound (2) and said compound (3), or a pharmaceutically acceptable salt thereof; or
    (b) said compound (4) and said compound (5), or a pharmaceutically acceptable salt thereof; or
    (c) said compound (2) and said compound (4), or a pharmaceutically acceptable salt thereof; or
    (d) said compound (3) and said compound (5), or a pharmaceutically acceptable salt thereof.

5. The method according to claim 1, wherein the central nervous system disorder is Parkinson's disease.

6. The method according to claim 1, wherein the central nervous system disorder is adrenoleukodystrophy (ALD or X-ALD).

7. The method according to claim 3, wherein the central nervous system disorder is Parkinson's disease lateral.

8. The method according to claim 3, wherein the central nervous system disorder is adrenoleukodystrophy (ALD or X-ALD).

9. The method according to claim 1, wherein no more than 1% of the total number of hydrogen atoms per mole of the compound of formula (1) are in the form of the $^2$H isotope.

10. The method according to claim 1, wherein the compound of formula (1) is administered to the subject in an oral dosage form.

11. The method according to claim 10, wherein the oral dosage form is an oral solution or an oral suspension.

12. The method according to claim 3, wherein no more than 1% of the total number of hydrogen atoms per mole of each of the two or more compounds in the mixture are in the form of the $^2$H isotope.

13. The method of claim 1, wherein the compound of formula (1) is administered at a dosage of from 0.1 mg to 200 mg.

14. The method of claim 13, wherein the dosage is from 10 mg to 100 mg.

15. The method of claim 1, wherein the compound of formula (1) is administered in a daily dose of from 80 mg to 600 mg.

16. The method of claim 1, wherein the central nervous system disorder is ALS.

17. The method of claim 1, wherein the central nervous system disorder is multiple sclerosis.

18. The method of claim 3, wherein the central nervous system disorder is ALS.

19. The method of claim 3, wherein the central nervous system disorder is multiple sclerosis.

20. The method of claim 10, wherein the oral dosage form is selected from the group consisting of tablets, capsules, pills, and granules.

21. The method of claim 1, wherein the dosage form is suitable for topical, epicutaneous, subcutaneous, transdermal, intramuscular, parenteral, ocular, rectal, vaginal, inhalation, buccal, sublingual or intranasal delivery.

22. The method of claim 21, wherein the dosage form is sublingual.

* * * * *

UNITED STATES PATENT AND TRADEMARK OFFICE
CERTIFICATE OF CORRECTION

PATENT NO. : 9,782,395 B2
APPLICATION NO. : 15/147484
DATED : October 10, 2017
INVENTOR(S) : García Collazo et al.

Page 1 of 2

It is certified that error appears in the above-identified patent and that said Letters Patent is hereby corrected as shown below:

In Column 5, Line 19, "the brain plasma ration" should read --the brain plasma ratio--.

In Column 5, Line 24, "the brain plasma ration" should read --the brain plasma ratio--.

In Column 16, Line 49, "(Scheme 45)" should read --(Scheme 5)--.

In Column 19, Line 44, in the beginning of the line, "NMR" should be added after "$^1$H".

In Column 24, Scheme 7, the first row,

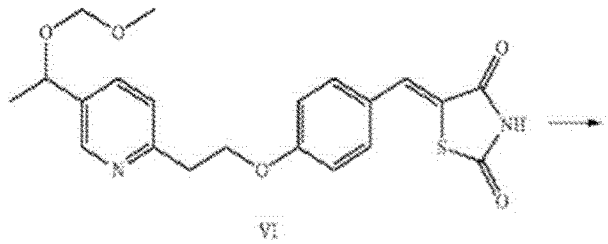

should appear as

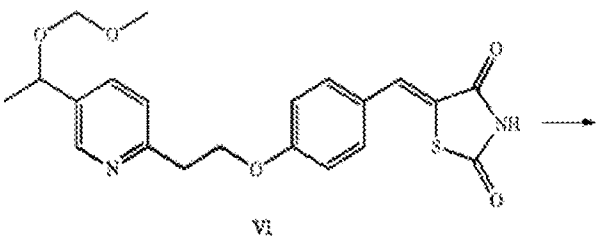

In Column 28, Line 5, the phrase "Pioglitazone, MII and MIII" should read --Pioglitazone, MIV, MII and MIII--.

Signed and Sealed this
Twentieth Day of November, 2018

Andrei Iancu
*Director of the United States Patent and Trademark Office*

Claim 7, Column 34, Line 62, the phrase "Parkinson's disease lateral" should read --Parkinson's disease--.